United States Patent
Krogh et al.

(10) Patent No.: US 8,586,828 B2
(45) Date of Patent: Nov. 19, 2013

(54) POLYPEPTIDES HAVING BETA-GLUCOSIDASE ACTIVITY AND POLYNUCLEOTIDES ENCODING SAME

(75) Inventors: Kristian Krogh, Bagsvaerd (DK); Paul Harris, Carnation, WA (US)

(73) Assignee: Novozymes A/S, Bagsvaerd (DK)

( * ) Notice: Subject to any disclaimer, the term of this patent is extended or adjusted under 35 U.S.C. 154(b) by 263 days.

(21) Appl. No.: 12/918,461

(22) PCT Filed: Mar. 6, 2009

(86) PCT No.: PCT/US2009/036341
§ 371 (c)(1),
(2), (4) Date: Nov. 18, 2010

(87) PCT Pub. No.: WO2009/111706
PCT Pub. Date: Sep. 11, 2009

(65) Prior Publication Data
US 2011/0131686 A1    Jun. 2, 2011

Related U.S. Application Data

(60) Provisional application No. 61/034,439, filed on Mar. 6, 2008.

(51) Int. Cl.
| C12P 21/02 | (2006.01) |
| C12N 15/56 | (2006.01) |
| C12N 15/82 | (2006.01) |
| C12N 9/42  | (2006.01) |
| A01N 63/00 | (2006.01) |

(52) U.S. Cl.
USPC .......... 800/284; 800/298; 435/200; 435/71.1; 424/93.2

(58) Field of Classification Search
None
See application file for complete search history.

(56) References Cited

U.S. PATENT DOCUMENTS

2006/0005279 A1* 1/2006 Dotson et al. ............ 800/284
2009/0038023 A1* 2/2009 Weiner et al. ............ 800/13

FOREIGN PATENT DOCUMENTS

| WO | WO 2004/099228 | 11/2004 |
| WO | WO 2007/019442 | 2/2007 |
| WO | WO 2007/071818 | 6/2007 |
| WO | WO 2007071818 A1 * | 6/2007 |

OTHER PUBLICATIONS

Guo et al. 2004. Protein tolerance to random amino acid change. PNAS. 101(25):9205-9210.*
Himmel et al. 2007. Biomass recalcitrance: Engineering plants and enzymes for biofuels production. Science. 315:804-807.*
Pozzo et al. 2010. Structural and functional analyses of beta-glucosidase 3B from *Thermotoga neapolitana*: A thermostable three-domain representative of glycoside hydrolase 3. J Mol Biol. 397:724-739.*
Jorgensen et al., Production of cellulases by *Penicillium brasilianum* IBT 20888—Effect of substrate on hydrolytic performance, Enzyme and Microbial Technology 38 (2006) 381-390.
Jorgensen et al., Purification and characterization of five cellulases and one xylanase from *Penicullium brasilianum* IBT 20888, Enzyme and Microbial Technology 32 (2003) 851-861.
Thygesen et al., Production of cellulose and hemicellulose-degrading enzymes by filamentous fungi cultivated on wet-oxidised wheat straw, Enzyme and Microbial Technology 32 (2003) 606-615.
Jorgensen et al., *Production of cellulases and hemicellulases by three Penicillium* species: effect of substrate and evaluation of cellulase adsorption by capillary electrophoresis, Enzyme and Microbial Technology, 36, 2005, 42-48.
Jorgensen et al., Growth and enzyme production by three *Penicillium* species on monosaccharides, Journal of Biotechnology 109 (2004) 295-299.
G. von Heijne, Protein targeting signals, Current Opinion in Cell Biology 1990, 2: 604-608.

* cited by examiner

*Primary Examiner* — Anne Kubelik
*Assistant Examiner* — Jeffrey Bolland
(74) *Attorney, Agent, or Firm* — Robert L. Starnes

(57) ABSTRACT

The present invention relates to isolated polypeptides having beta-glucosidase activity and isolated polynucleotides encoding the polypeptides. The invention also relates to nucleic acid constructs, vectors, and host cells comprising the polynucleotides as well as methods of producing and using the polypeptides.

26 Claims, 1 Drawing Sheet

```
ATGAAGCTCGGGTGGCTGGAAGCCACCGTCCTCACGACCGCAACGGTCGCCAGTGCTAAGGTTTGTCACTCCATGAGCG    79
  M  K  L  G  W  L  E  A  T  V  L  T  T  A  T  V  A  S  A  K
TAGAGTATATCTTGCCATAGCCGATGCCTTCATCTCCGTTTTAGCAAGAACTAATTGAAGCCTTTTCTCATAGGACCCTC   158
                                                                              D  L
GCATACTCCCCTCCCTATTACCCGTCCCCATGGGCTACCGGCGAAGGCGACTGGGCCTCGGCCTATCGGCGGCCGTGG    237
  A  Y  S  P  P  Y  Y  P  S  P  W  A  T  G  E  G  D  W  A  S  A  Y  R  R  A  V
ATTTCGTCTCTAATTTGACTCTGGCGGAGAAGGTCAATTTGACAACCGGTGCTGGGTATGTGATTCATAACGTCGAGAT   316
 D  F  V  S  N  L  T  L  A  E  K  V  N  L  T  T  G  A  G
TGCATGACGAAGAGAAATTGGTATTAACAGCTTACGTAGATGGGAGCAAGAACACTGTGTCGGTGAGACCGGTGGTATC   395
                                           W  E  Q  E  H  C  V  G  E  T  G  G  I
CCCAGGTAAGATCGCGCGACACGCCAAAGCCAACGATGAGAAAGAGTCAAAGCCATTGACAGGTGAGGATGAAATAGAC   474
 P  R
TTGGAATGTGGGAATGTGTATGCAAGATTCACCCCTCGGTGTTCGTAACGGTATGGCGATCCCGCTCTTGTCAATATC    553
  L  G  M  W  G  M  C  M  Q  D  S  P  L  G  V  R  N
GAAATGAACTAATGGAATCTCCACAGCCGATTACAACTCGGGTTTCCCGGCCGGTGTCAATGTGGCCGCGACCTGGGAT   632
                                         A  D  Y  N  S  G  F  P  A  G  V  N  V  A  A  T  W  D
AAGCAACTTGCCTACCAACGTGGTGTGGCAATGGGCGAGGAGCACCGTGACAAAGGCGTTGATGTTCAGCTTGGACCGG   711
 K  Q  L  A  Y  Q  R  G  V  A  M  G  E  E  H  R  D  K  G  V  D  V  Q  L  G  P
TCGCAGGCCCCCTGGGCAAATACCCCGACGGTGGTCGTAACTGGGAAGGATTTGCGCCCGATCCCGTCCTGACTGGTGT   790
  V  A  G  P  L  G  K  Y  P  D  G  G  R  N  W  E  G  F  A  P  D  P  V  L  T  G  V
GATGATGGCCGAGACCATCAAGGGTATCCAAGATGCTGGTGTCATTGCTTGCGCCAAGCACTTTATCGGCAATGAGCAG   869
  M  M  A  E  T  I  K  G  I  Q  D  A  G  V  I  A  C  A  K  H  F  I  G  N  E  Q
GAGCACTTCCGCCAGGCCGGCGAGGCTCAGGGATATGGATACAATATCACCGAGAGTGTCAGCGCCAACATCGATGACA   948
   E  H  F  R  Q  A  G  E  A  Q  G  Y  G  Y  N  I  T  E  S  V  S  A  N  I  D  D
AGACCATGCACGAGCTGTACCTCTGGCCCTTTGTCGACTCCGTCCGTGCCGGTGTCGGCTCCGTCATGTGCTCGTACAA  1027
 K  T  M  H  E  L  Y  L  W  P  F  V  D  S  V  R  A  G  V  G  S  V  M  C  S  Y  N
CCAAATCAACAACAGCTACGGCTGCTCTAACAGCTACACCCTCAACAAGTCCTC                           1081
   Q  I  N  N  S  Y  G  C  S  N  S  Y  T  L  N  K  S  S
```

SEQUENCE LISTING

```
<160> NUMBER OF SEQ ID NOS: 6

<210> SEQ ID NO 1
<211> LENGTH: 1081
<212> TYPE: DNA
<213> ORGANISM: Penicillium brasilianum

<400> SEQUENCE: 1
atgaagctcg gtggctgga agccaccgtc ctcacgaccg caacggtcgc cagtgctaag      60
gtttgtcact ccatgagcgt agagtatatc ttgccatagc cgatgccttc atctccgttt    120
tagcaagaac taattgaagc cttttctcat aggacctcgc atactcccct ccctattacc    180
cgtccccatg ggctaccggc gaaggcgact gggcctcggc ctatcggcgg gccgtggatt    240
tcgtctctaa tttgactctg gcggagaagg tcaatttgac aaccggtgct gggtatgtga    300
ttcataacgt cgagattgca tgacgaagag aaattggtat taacagctta cgtagatggg    360
agcaagaaca ctgtgtcggt gagaccggtg gtatccccag gtaagatcgc gcgacacgcc    420
aaagccaacg atgagaaaga gtcaaagcca ttgacaggtg aggatgaaat agacttggaa    480
tgtggggaat gtgtatgcaa gattcacccc tcggtgttcg taacggtatg gcgatcccgc    540
tcttgtcaat atcgaaatga actaatggaa tctccacagc cgattacaac tcgggtttcc    600
cggccggtgt caatgtggcc gcgacctggg ataagcaact tgcctaccaa cgtggtgtgg    660
caatgggcga ggagcaccgt gacaaaggcg ttgatgttca gcttggaccg gtcgcaggcc    720
```

```
ccctgggcaa ataccccgac ggtggtcgta actgggaagg atttgcgccc gatcccgtcc      780
tgactggtgt gatgatggcc gagaccatca agggtatcca agatgctggt gtcattgctt      840
gcgccaagca ctttatcggc aatgagcagg agcacttccg ccaggccggc gaggctcagg      900
gatatggata caatatcacc gagagtgtca gcgccaacat cgatgacaag accatgcacg      960
agctgtacct ctggcccttt gtcgactcgg tccgtgccgg tgtcggctcc gtcatgtgct     1020
cgtacaacca aatcaacaac agctacggct gctctaacag ctacaccctc aacaagtcct     1080
c                                                                    1081
```

<210> SEQ ID NO 2
<211> LENGTH: 267
<212> TYPE: PRT
<213> ORGANISM: Penicillium brasilianum

<400> SEQUENCE: 2

```
Met Lys Leu Gly Trp Leu Glu Ala Thr Val Leu Thr Thr Ala Thr Val
1               5                   10                  15

Ala Ser Ala Lys Asp Leu Ala Tyr Ser Pro Pro Tyr Tyr Pro Ser Pro
            20                  25                  30

Trp Ala Thr Gly Glu Gly Asp Trp Ala Ser Ala Tyr Arg Arg Ala Val
        35                  40                  45

Asp Phe Val Ser Asn Leu Thr Leu Ala Glu Lys Val Asn Leu Thr Thr
    50                  55                  60

Gly Ala Gly Trp Glu Gln Glu His Cys Val Gly Glu Thr Gly Gly Ile
65                  70                  75                  80

Pro Arg Leu Gly Met Trp Gly Met Cys Met Gln Asp Ser Pro Leu Gly
                85                  90                  95

Val Arg Asn Ala Asp Tyr Asn Ser Gly Phe Pro Ala Gly Val Asn Val
            100                 105                 110

Ala Ala Thr Trp Asp Lys Gln Leu Ala Tyr Gln Arg Gly Val Ala Met
        115                 120                 125

Gly Glu Glu His Arg Asp Lys Gly Val Asp Val Gln Leu Gly Pro Val
    130                 135                 140

Ala Gly Pro Leu Gly Lys Tyr Pro Asp Gly Gly Arg Asn Trp Glu Gly
145                 150                 155                 160

Phe Ala Pro Asp Pro Val Leu Thr Gly Val Met Met Ala Glu Thr Ile
                165                 170                 175

Lys Gly Ile Gln Asp Ala Gly Val Ile Ala Cys Ala Lys His Phe Ile
            180                 185                 190

Gly Asn Glu Gln Glu His Phe Arg Gln Ala Gly Glu Ala Gln Gly Tyr
        195                 200                 205

Gly Tyr Asn Ile Thr Glu Ser Val Ser Ala Asn Ile Asp Asp Lys Thr
    210                 215                 220

Met His Glu Leu Tyr Leu Trp Pro Phe Val Asp Ser Val Arg Ala Gly
225                 230                 235                 240

Val Gly Ser Val Met Cys Ser Tyr Asn Gln Ile Asn Asn Ser Tyr Gly
                245                 250                 255

Cys Ser Asn Ser Tyr Thr Leu Asn Lys Ser Ser
            260                 265
```

<210> SEQ ID NO 3
<211> LENGTH: 32
<212> TYPE: DNA
<213> ORGANISM: Penicillium brasilianum
<220> FEATURE:

```
<221> NAME/KEY: misc_feature
<222> LOCATION: (24)..(24)
<223> OTHER INFORMATION: N=A,C,G, OR T
<220> FEATURE:
<221> NAME/KEY: misc_feature
<222> LOCATION: (30)..(30)
<223> OTHER INFORMATION: N=A,C,G, OR T

<400> SEQUENCE: 3
tctcctcctt actacccttc tccntgggcn ac                                32

<210> SEQ ID NO 4
<211> LENGTH: 27
<212> TYPE: DNA
<213> ORGANISM: Penicillium brasilianum
<220> FEATURE:
<221> NAME/KEY: misc_feature
<222> LOCATION: (19)..(19)
<223> OTHER INFORMATION: N=A,C,G, OR T
<220> FEATURE:
<221> NAME/KEY: misc_feature
<222> LOCATION: (20)..(20)
<223> OTHER INFORMATION: K=G OR T
<220> FEATURE:
<221> NAME/KEY: misc_feature
<222> LOCATION: (22)..(22)
<223> OTHER INFORMATION: R=A OR G
<220> FEATURE:
<221> NAME/KEY: misc_feature
<222> LOCATION: (25)..(25)
<223> OTHER INFORMATION: N=A,C,G, OR T

<400> SEQUENCE: 4
gtcggtcatg acgaagccnk graancc                                      27

<210> SEQ ID NO 5
<211> LENGTH: 25
<212> TYPE: DNA
<213> ORGANISM: Penicillium brasilianum

<400> SEQUENCE: 5
cttggtaccg agctcggatc cacta                                        25

<210> SEQ ID NO 6
<211> LENGTH: 25
<212> TYPE: DNA
<213> ORGANISM: Penicillium brasilianum

<400> SEQUENCE: 6
atagggcgaa ttgggccctc tagat                                        25
```

US 8,586,828 B2

POLYPEPTIDES HAVING BETA-GLUCOSIDASE ACTIVITY AND POLYNUCLEOTIDES ENCODING SAME

CROSS-REFERENCE TO RELATED APPLICATIONS

This application is a 35 U.S.C. 371 national application of PCT/US2009/036341 filed on Mar. 6, 2009, which claims priority from U.S. provisional application Ser. No. 61/034,439 filed on Mar. 6, 2008. The contents of these applications are fully incorporated herein by reference.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to isolated polypeptides having beta-glucosidase activity and isolated polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of the simple sugar glucose linked by beta-1,4 bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol. Since glucose is readily fermented to ethanol by a variety of yeasts while cellobiose is not, any cellobiose remaining at the end of the hydrolysis represents a loss of yield of ethanol. More importantly, cellobiose is a potent inhibitor of endoglucanases and cellobiohydrolases. The accumulation of cellobiose during hydrolysis is undesirable for ethanol production.

Cellobiose accumulation has been a major problem in enzymatic hydrolysis because cellulase-producing microorganisms may produce little beta-glucosidase. The low amount of beta-glucosidase results in a shortage of capacity to hydrolyze the cellobiose to glucose. Several approaches have been used to increase the amount of beta-glucosidase in cellulose conversion to glucose.

One approach is to produce beta-glucosidase using microorganisms that produce little cellulase, and add the beta-glucosidase exogenously to endoglucanases and cellobiohydrolase to enhance the hydrolysis.

A second approach is to carry out cellulose hydrolysis simultaneously with fermentation of the glucose by yeast. This process is known as simultaneous saccharification and fermentation (SSF). In an SSF system, fermentation of the glucose removes it from solution. However. SSF systems are not yet commercially viable because the operating temperature for yeast of 28° C. is too low for the 50° C. conditions required.

A third approach to overcome the shortage of beta-glucosidase is to overexpress the beta-glucosidase in a host, thereby increasing the yield of beta-glucosidase.

Jørgensen et al., 2003, *Enzyme and Microbial Technology* 32: 851-861. Thygesen et al., 2003, *Enzyme and Microbial Technology* 32: 606-615, Jørgensen et al., 2004, *Journal of Biiotechnolooy* 109: 295-299, and Jørgensen and Olsson, 2006, *Enzyme and Microbial Technology* 38: 381-390 disclose cellulose-degrading enzymes from *Penicillium brasilianum* IBT 20888.

It would be an advantage in the art to provide new beta-glucosidases with improved properties for converting cellulosic materials to monosaccharides, disaccharides, and polysaccharides.

The present invention provides polypeptides having beta-glucosidase activity and polynucleotides encoding the polypeptides.

SUMMARY OF THE INVENTION

The present invention relates to isolated polypeptides having beta-glucosidase activity selected from the group consisting of:

(a) a polypeptide comprising an amino acid sequence comprising a partial amino acid sequence having at least 75% identity to the partial amino acid sequence of amino acids 20 to 267 of SEQ ID NO: 2;

(b) a polypeptide encoded by a polynucleotide comprising a nucleotide sequence comprising a partial nucleotide sequence that hybridizes under at least high stringency conditions with (i) the partial nucleotide sequence of nucleotides 58 to 1081 of SEQ ID NO: 1, (ii) the cDNA sequence contained in the partial nucleotide sequence of nucleotides 58 to 1081 of SEQ ID NO: 1, or (iii) a full-length complementary strand of (i) or (ii):

(c) a polypeptide encoded by a polynucleotide comprising a nucleotide sequence comprising a partial nucleotide sequence having at least 75% identity to the partial nucleotide sequence of nucleotides 58 to 1081 of SEQ ID NO: 1; and (d) a variant comprising an amino acid sequence comprising a substitution, deletion, and/or insertion of one or more (several) amino acids of the partial amino acid sequence of amino acids 20 to 267 of SEQ ID NO: 2.

The present invention also relates to isolated polynucleotides encoding polypeptides having beta-glucosidase activity, selected from the group consisting of:

(a) a polynucleotide encoding a polypeptide comprising an amino acid sequence comprising a partial amino acid sequence having at least 75% identity to the partial amino acid sequence of amino acids 20 to 267 of SEQ ID NO: 2:

(b) a polynucleotide comprising a nucleotide sequence comprising a partial nucleotide sequence that hybridizes under at least high stringency conditions with (i) the partial nucleotide sequence of nucleotides 58 to 1081 of SEQ ID NO: 1, (ii) the cDNA sequence contained in the partial nucleotide sequence of nucleotides 58 to 1081 of SEQ ID NO: 1, or (iii) a full-length complementary strand of (i) or (ii);

(c) a polynucleotide comprising a nucleotide sequence comprising a partial nucleotide sequence having at least 75% identity to the partial nucleotide sequence of nucleotides 58 to 1081 of SEQ ID NO: 1; and (d) a polynucleotide encoding a variant comprising an amino acid sequence comprising a substitution, deletion, and/or insertion of one or more (several) amino acids of the partial amino acid sequence of amino acids 20 to 267 of SEQ ID NO: 2.

The present invention also relates to nucleic acid constructs, recombinant expression vectors, recombinant host cells comprising the polynucleotides, and methods of producing a polypeptide having beta-glucosidase activity.

The present invention also relates to methods of inhibiting the expression of a polypeptide having beta-glucosidase activity in a cell, comprising administering to the cell or expressing in the cell a double-stranded RNA (dsRNA) molecule, wherein the dsRNA comprises a subsequence of a polynucleotide of the present invention. The present also relates to such a double-stranded inhibitory RNA (dsRNA) molecule, wherein optionally the dsRNA is a siRNA or a miRNA molecule.

The present invention also relates to methods of using the polypeptides having beta-glucosidase activity in the conversion of cellulose to glucose and various substances.

The present invention also relates to plants comprising an isolated polynucleotide encoding a polypeptide having beta-glucosidase activity.

The present invention also relates to methods of producing a polypeptide having beta-glucosidase activity, comprising: (a) cultivating a transgenic plant or a plant cell comprising a polynucleotide encoding the polypeptide having beta-glucosidase activity under conditions conducive for production of the polypeptide; and (b) recovering the polypeptide.

The present invention further relates to an isolated polynucleotide encoding a signal peptide comprising or consisting of amino acids 1 to 19 of SEQ ID NO: 2; to nucleic acid constructs, expression vectors, and recombinant host cells comprising the polynucleotide; and to methods of producing a protein.

BRIEF DESCRIPTION OF THE FIGURES

FIG. 1 shows the partial genomic DNA sequence and the deduced amino acid sequence of a *Penicillium brasilianum* IBT 20888 Family 3 beta-glucosidase (SEQ ID NOs: 1 and 2, respectively).

DEFINITIONS

Beta-glucosidase activity: The term "beta-glucosidase activity" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et at, 2002, *J. Basic Microbiol.* 42: 55-66, except different conditions were employed as described herein. One unit of beta-glucosidase activity is defined as 1.0 µmole of 4-nitrophenol produced per minute at 25° C., pH 4,8 from 1 mM 4-nitrophenyl-beta-D-glucopyranoside as substrate in 50 mM sodium citrate. Methyl-umbelliferyl glucoside can also be used a substrate as described in the Examples.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the beta-glucosidase activity of a polypeptide comprising an amino acid sequence comprising the partial amino acid sequence of amino acids 20 to 267 of SEQ ID NO: 2.

Endoglucanase activity: The term "endoglucanase activity" is defined herein as an endo-1,4-beta-D-glucan 4-glucanohydrolase (E.C. No. 3.2.1.4) that catalyses the endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268. One unit of endoglucanase activity is defined as 1.0 µmole of reducing sugars produced per minute at 50° C., pH 4.8.

Cellobiohydrolase: The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain. For purposes of the present invention, cellobiohydrolase activity is determined according to the procedures described by Lever et at, 1972, *Anal. Biochem.* 47: 273-279 and by van Tilbeurgh et al., 1982, *FEBS Letters* 149: 152-156, van Tilbeurgh and Claeyssens, 1985, *FEBS Letters* 187: 283-288. In the present invention, the Lever at al. method was employed to assess hydrolysis of cellulose in corn stover, while the method of van Tilbeurgh at al. was used to determine the cellobiohydrolase activity on a fluorescent disaccharide derivative.

Family 3 glycoside hydrolase or Family GH3 or GH3: The term "Family 3 glycoside hydrolase" or "Family GH3" or "GH3" is defined herein as a polypeptide falling into the glycoside hydrolase Family 3 according to Henrissat B., 1991, A classification of glycoside hydrolases based on amino-acid sequence similarities, *Biochem. J.* 280: 309-316, and Henrissat B., and Bairoch A., 1996, Updating the sequence-based classification of glycoside hydrolases, *Biochem. J.* 316: 695-696.

Family 61 glycoside hydrolase or Family 61 or GH61: The term "Family 61 glycoside hydrolase" or "Family GH61" or "GH61" is defined herein as a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. Presently, Henrissat lists the GH61 Family as unclassified indicating that properties such as mechanism, catalytic nucleophile/base, and catalytic proton donors are not known for polypeptides belonging to this family.

Cellulosic material: The predominant polysaccharide in the primary cell wall of biomass is cellulose, the second most abundant is hemi-cellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

The cellulosic material can be any material containing cellulose. Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue The cellulosic material can be any type of biomass including, but not limited to wood resources, municipal solid waste, wastepaper, crops, and crop residues (see, for example, Wiselogel et al, 1995, in Handbook on Bioethanol (Charles E. Wyman, editor), pp. 105-118. Taylor & Francis, Washington D.C.; Wyman, 1994, *Bioresource Technology* 50: 3-16: Lynd, 1990, *Applied Biochemistry and Biotechnology* 24/25: 695-719: Mosier et al., 1999. Recent Progress in Bioconversion of Lignocellulosics, in *Advances in Biochemical Engineering/Biotechnology*, T. Scheper, managing editor, Volume 65, pp. 23-40. Springer-Verlag, New York). It is understood herein that the cellulose may be in the form of lignocellulose, a plant cell wall material containing lignin, cellulose, and hemicellulose in a mixed matrix.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another preferred aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse.

The cellulosic material may be used as is or may be subjected to pretreatment, using conventional methods known in the art. For example, physical pretreatment techniques can include various types of milling, irradiation, steaming/steam explosion, and hydrothermolysis: chemical pretreatment techniques can include dilute acid, alkaline, organic solvent, ammonia, sulfur dioxide, carbon dioxide, and pH-controlled hydrothermolysis; and biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh, P., and Singh, A., 1993, Physicochemical and biological treatments for enzymatic/microbial conversion of lignocellulosic biomass, *Adv. Appl. Microbiol* 39: 295-333; McMillan, J. D., 1994. Pretreating lignocellulosic biomass: a review, in *Enzymatic Conversion of Biomass for Fuels Production*, Himmel, M. E., Baker, J. O., and Overend, R, P., eds., ACS Symposium Series 566, American Chemical Society, Washington, D.C., chapter 15; Gong, C. S., Cao, N. J., Du, J., and Tsao, G. T., 1999. Ethanol production from renewable resources, in *Advances in Biochemical Engineering/Biotechnology*, Scheper. T., ed., Springer-Verlag Berlin Heidelberg, Germany, 65: 207-241: Olsson, L., and Hahn-Hagerdai, B., 1996, Fermentation of lignocellulosic hydrolysates for ethanol production, *Enz. Microb. Tech,* 18: 312-331; and Vallander, L., and Eriksson, K.-E. L., 1990, Production of ethanol from lignocellulosic materials: State of the art, *Adv. Biochem. Eng./Biotechnol.* 42: 63-95).

Pretreated corn stover: The term "PCS" or "Pretreated Corn Stover" is defined herein as a cellulosic material derived from corn stover by treatment with heat and dilute acid.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having beta-glucosidase activity that is in its final form following translation and any post-translational modifications, such as N-terminal processing, C-terminal truncation, glycosylation, phosphorylation, etc.

Mature polypeptide coding sequence: The term "mature polypeptide coding sequence" is defined herein as a nucleotide sequence that encodes a mature polypeptide having beta-glucosidase activity.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of identity between two deoxyribonucleotide sequences is determined using the Needleman-Wunsch algorithm (Needleman and Wunsch, 1970, supra as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the partial amino acid sequence of amino acids 20 to 267 of SEQ ID NO: 2.

Polypeptide fragment: The term "polypeptide fragment" is defined herein as a polypeptide having one or more (several) amino acids deleted from the amino and/or carboxyl terminus of an amino acid sequence comprising the partial amino acid sequence of amino acids 20 to 267 of SEQ ID NO: 2; or a homologous sequence thereof; wherein the fragment has beta-glucosidase activity.

Subsequence: The term "subsequence" is defined herein as a nucleotide sequence having one or more (several) nucleotides deleted from the 5' and/or 3' end of a nucleotide sequence comprising the partial nucleotide sequence of nucleotides 58 to 1081 of SEQ ID NO: 1; or a homologous sequence thereof; wherein the subsequence encodes a polypeptide fragment having beta-glucosidase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of a polynucleotide sequence such that the control sequence directs the expression of the coding sequence of a polypeptide.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of a polypeptide comprising an amino acid sequence comprising the partial amino acid sequence of amino acids 20 to 267 of SEQ ID NO: 2: or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having beta-glucosidase activity produced by an organism expressing a modified polynucleotide sequence comprising a nucleotide sequence comprising the partial nucleotide sequence of nucleotides 58 to 1081 of SEQ ID NO: 1; or a homologous sequence thereof. The modified nucleotide sequence is obtained through human intervention by modification of the polynucleotide sequence comprising the partial nucleotide sequence of nucleotides 58 to 1081 of SEQ ID NO: 1; or a homologous sequence thereof.

DETAILED DESCRIPTION OF THE INVENTION

Polypeptides Having Beta-Glucosidase Activity

In a first aspect, the present invention relates to isolated polypeptides comprising amino acid sequences comprising partial amino acid sequences having a degree of identity to the partial amino acid sequence of amino acids 20 to 267 of SEQ ID NO: 2 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In a preferred aspect, the homologous polypeptides comprise amino acid sequences comprising partial amino acid sequences that differ by ten amino acids, preferably by five amino acids, more preferably by four amino acids, even more preferably by three amino acids, most preferably by two amino acids, and even most preferably by one amino acid from the partial amino acid sequence of amino acids 20 to 267 of SEQ ID NO; 2.

In a preferred aspect, the polypeptide comprises an amino acid sequence comprising the partial amino acid sequence of amino acids 20 to 267 of SEQ ID NO: 2, or an allelic variant thereof; or a fragment thereof having beta-glucosidase activity. In another preferred aspect, the polypeptide comprises an amino acid sequence comprising the partial amino acid sequence of amino acids 20 to 267 of SEQ ID NO: 2.

In a second aspect, the present invention relates to isolated polypeptides having beta-glucosidase activity that are encoded by polynucleotides comprising nucleotide sequences comprising partial nucleotide sequences that hybridize under preferably very low stringency conditions, more preferably low stringency conditions, more preferably medium stringency conditions, more preferably medium-high stringency conditions, even more preferably high stringency conditions, and most preferably very high stringency conditions with (i) the partial nucleotide sequence of nucleotides 58 to 1081 of SEQ ID NO: 1, (ii) the cDNA sequence contained in the partial nucleotide sequence of nucleotides 58 to 1081 of SEQ ID NO: 1, (iii) a subsequence of (i) or (ii), or (iv) a full-length complementary strand of (i), (ii), or (iii) (J. Sambrook. E. F. Fritsch, and T. Maniatis, 1989, *Molecular Cloning, A Laboratory Manual,* 2d edition, Cold Spring Harbor, N.Y.). A subsequence of the partial nucleotide sequence of nucleotides 58 to 1081 of SEQ ID NO: 1 contains at least 100 contiguous nucleotides or preferably at least 200 contiguous nucleotides. Moreover, the subsequence may encode a polypeptide fragment having beta-glucosidase activity. In a preferred aspect, the complementary strand is the full-length complementary strand of the partial nucleotide sequence of nucleotides 58 to 1081 of SEQ ID NO: 1.

The nucleotide sequence of nucleotides 58 to 1081 of SEQ ID NO: 1; or a subsequence thereof; as well as the amino acid sequence of amino acids 20 to 267 of SEQ ID NO: 2; or a fragment thereof; may be used to design nucleic acid probes to identify and clone DNA encoding polypeptides having beta-glucosidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides in length, Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having beta-glucosidase activity. Genomic or other DNA from such other strains may be separated by agarose or polyacrylamide gel electrophoresis, or other separation techniques, DNA from the libraries or the separated DNA may be transferred to and immobilized on nitrocellulose or other suitable carrier material. In order to identify a clone or DNA that is homologous with nucleotides 58 to 1081 of SEQ ID NO: 1; or a subsequence thereof: the carrier material is preferably used in a Southern blot.

For purposes of the present invention, hybridization indicates that the nucleotide sequence hybridizes to a labeled nucleic acid probe corresponding to the partial nucleotide sequence of nucleotides 58 to 1081 of SEQ ID NO: 1: the cDNA sequence contained in the partial nucleotide sequence of nucleotides 58 to 1081 of SEQ ID NO: 1: its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the partial nucleotide sequence of nucleotides 58 to 1081 of SEQ ID NO: 1 or a subsequence thereof. In another preferred aspect, the nucleic acid probe is the partial nucleotide sequence of nucleotides 58 to 1081 of SEQ ID NO: 1. In another preferred aspect, the nucleic acid probe is a nucleotide sequence that encodes the partial amino acid sequence of amino acids 20 to 267 of SEQ ID NO: 2 or a subsequence thereof. In another preferred aspect, the nucleic acid probe is a nucleotide sequence that encodes the partial amino acid sequence of amino acids 20 to 267 of SEQ ID NO: 2.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SOS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate. 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having beta-glucosidase activity encoded by polynucleotides comprising nucleotide sequences comprising partial nucleotide sequences that have a degree of identity to the partial nucleotide sequence of nucleotides 58 to 1081 of SEQ ID NO: 1 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity. See polynucleotide section herein.

In a fourth aspect, the present invention relates to artificial variants comprising an amino acid sequence comprising a substitution, deletion, and/or insertion of one or more (or several) amino acids of the partial amino acid sequence of amino acids 20 to 267 of SEQ ID NO: 2; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues: or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues, "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., bata-glucosidase activity) to identify amino acid residues that are critical to the activity of the molecule, See also, Hilton et at, 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett*, 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156: WO 95/17413; or WO 95/22625. Other methods that can be used include error-prone PCR, phage display (e.g., Lowman et al., 1991, *Biochem.* 30: 10832-10837; U.S. Pat. No. 5,223, 409; WO 92/06204), and region-directed mutagenesis (Derbyshire at al., 1986, *Gene* 46; 145; Ner at al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids 20 to 267 of the partial amino acid sequence of SEQ ID NO: 2 is 10, preferably 9, more preferably 8, more preferably 7, more preferably at most 6, more preferably 5, more preferably 4, even more preferably 3, most preferably 2, and even most preferably 1.

Sources of Polypeptides Having Beta-Glucosidase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having beta-glucosidase activity of the present invention may be a bacterial polypeptide. For example, the polypeptide may be a gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, or *Oceanobacillus* polypeptide having beta-glucosidase activity, or a Gram negative bacterial polypeptide such as an *E. coli*, *Pseudomonas*, *Salmonella*, *Campylobacter Helicobacter*, *Flavobacterium*, *Fusobacterium*, *Ilyobacter*, *Neisseria*, or *Ureaplasma* polypeptide having beta-glucosidase activity.

In a preferred aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having beta-glucosidase activity.

In another preferred aspect, the polypeptide is a *Streptococcus equisimilis*, *Streptococcus pyogenes*, *Streptococcus uberis*, or *Streptococcus equi* subsp. *Zooepidemicus* polypeptide having beta-glucosidase activity.

In another preferred aspect, the polypeptide is a *Streptomyces achromogenes*, *Streptomyces averrnitilis*, *Streptomyces coeficolor*, *Streptomyces griseus*, or *Streptomyces lividans* polypeptide having beta-glucosidase activity.

A polypeptide having beta-glucosidase activity of the present invention may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having beta-glucosidase activity; or more preferably a filamentous fungal polypeptide such as an *Acremonium*, *Agaricus*, *Alternaria*, *Aspergillus*, *Aureobasidium*, *Botryospaeria*, *Ceriporiopsis*, *Chaetornidium*, *Chrysosporium*, *Claviceps*, *Cochliobolus*, *Coprinopsis*, *Coptotermies*, *Corynascus*, *Cryphonectria*, *Ctyptococcus*, *Diplodia*, *Exidia*, *Filibasidium*, *Fusarium*, *Gibberella*, *Holomastigotaides*, *Humicola*, *Irpex*, *Lentinula*, *Leptospaeria*, *Magnaporthe*, *Melanocarpus*, *Meripilus*, *Mucor*, *Myceliophthora*, *Neocailimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Totypocladium*, *Trichoderma*, *Trichophaea*, *Verticillium*, *Volvariella*, or *Xylaria* polypeptide having beta-glucosidase activity.

In a preferred aspect, the polypeptide is a *Saccharomyces carlsbergensis*, *Saccharomyces cerevisiae*, *Saccharomyces diastaticus*, *Saccharomyces Saccharomyces kluyveri*, *Saccharomyces norbensis*, or *Saccharomyces oviformis* polypeptide having beta-glucosidase activity.

In another preferred aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophifum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torufosum*, *Fusarium trichothecioides*, *Fusarium venenatum*, *Humicola grisea*, *Humicola insofens*, *Humicola lanuginosa*, *Irpex lacteus*, *Mucor miehei*, *Myoehophthora thermophila*, *Neurospora crassa*, *Phanerochaete chrysosporium*, *Thielavia achromatica*, *Thiefavia albomyces*, *Thielavia aibopilosa*, *Thielavia australeinsis*, *Thielavia Thielavia microspora*, *Thielavia ovispora*, *Thielavia peruviana*, *Thielavia spededonturn*, *Thielavia setosa*, *Thielavia subtherrnophila*, *Thielavia terrestris*, *Trichoderma harzianum*, *Trichoderma lconingii*, *Trichoderma longibrachiatum*, *Trichoderma reesei*, or *Trichoderma virile* polypeptide having beta-glucosidase activity.

In another preferred aspect, the polypeptide is a *Penicillium brasilianum*, *Penicillium camembertii*, *Penicillium capsulatum*, *Penicillium chrysogenum*, *Penicillium citreonigrum*, *Penicillium citrinum*, *Penicillium claviforme*, *Penicillium corylophilum*, *Penicillium crustosum*, *Penicillium digitatum*, *Penicillium expansum*, *Penicillium funiculosum*, *Penicellium glabrum*, *Penicillium granulatum*, *Penicillium griseofulvum*, *Penicillium islandicum*, *Penicellium italicum*, *Penicillium janthinellum*, *Penicillium lividum*, *Penicillium megasporum*, *Peniallium mehnii*, *Penicillium notatum*, *Penicillium oxalicum*, *Penicillium puberulum*, *Penicillium purpurescens*, *Penicillium purpurogenum*, *Penicillium roquefortif*, *Penicillium rugulosum*, *Penicillium spinulosurn*, *Penicillium waksmanii*, or *Penicillium* sp. polypeptide having beta-glucosidase activity.

In a more preferred aspect, the polypeptide is a *Penicillium brasilianum* polypeptide having beta-glucosidase activity, and most preferably a *Penicillium brasilianum* IBT 20888 polypeptide having beta-glucosidase activity.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zelikulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having beta-glucosidase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-576; Svetina et at, 2000. *J. Biotechnol.* 76: 245-251; Rasmussen-Wilson et al., 1997, *Appl. Environ. Microbiol.* 63: 3488-3493: Ward et al., 1995, *Biotechnology* 13: 498-503; and Contreras at al., 1991, *Biotechnology* 9: 378-381), an Ile-(Glu Asp)-Gly-Arg site, which is cleaved by a Factor Xa protease after the arginine residue (Eaton at al., 1986, *Biochem.* 25: 505-512): a Asp-Asp-Asp-Asp-Lys site, which is cleaved by an enterokinase after the lysine (Collins-Racie et al., 1995, *Biotechnology* 13: 982-987): a His-Tyr-Glu site or His-Tyr-Asp site, which is cleaved by Genenase I (Carter at al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48): a Glu-Asn-Leu-Tyr-Phe-Gln-Gly site, which is cleaved by TEV protease after the Gln (Stevens, 2003, supra): and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising nucleotide sequences that encode polypeptides having beta-glucosidase activity of the present invention.

In a preferred aspect, the polynucleotide comprises a nucleotide sequence comprising the partial nucleotide sequence of nucleotides 58 to 1081 of SEQ ID NO: 1 or a subsequence thereof that encodes a polypeptide fragment having beta-glucosidase activity. In another preferred aspect, the polynucleotide comprises a nucleotide sequence comprising the partial nucleotide sequence of nucleotides 58 to 1081 of SEQ ID NO: 1. The present invention also encompasses nucleotide sequences that encode polypeptides comprising amino acid sequences comprising the partial amino acid sequence of amino acids 20 to 267 of SEQ ID NO: 2, which differ from the partial nucleotide sequence of nucleotides 58 to 1081 of SEQ ID NO: 1 by virtue of the degeneracy of the genetic code.

The present invention also relates to mutant polynucleotides comprising nucleotide sequences comprising partial nucleotide sequences comprising at least one mutation in the partial nucleotide sequence of nucleotides 58 to 1081 of SEQ ID NO: 1, in which the mutant nucleotide sequence encodes a polypeptide comprising an amino acid sequence comprising the partial amino acid sequence of amino acids 20 to 267 of SEQ ID NO: 2, respectively.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected. e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Penicillium*, or another or related organism and thus, for example, may be an allelic or species variant of the polypeptide encoding region of the nucleotide sequence.

The present invention also relates to isolated polynucleotides comprising nucleotide sequences comprising partial nucleotide sequences having a degree of identity to the partial nucleotide sequence of nucleotides 58 to 1081 of SEQ ID NO: 1 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity, which encode a polypeptide having beta-glucosidase activity.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of a nucleotide sequence comprising the partial nucleotide sequence of SEQ ID NO: 1 or the partial nucleotide sequence of SEQ ID NO 3, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for beta-glucosidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra: Smith et al., 1992. supra; Wlodaver et al., 1992, supra).

The present invention also relates to isolated polynucleotides, encoding polypeptides of the present invention, comprising nucleotide sequences comprising partial nucleotide sequences that hybridize under very low stringency conditions, preferably low stringency conditions, more preferably medium stringency conditions, more preferably medium-high stringency conditions, even more preferably high stringency conditions, and most preferably very high stringency conditions with (i) the partial nucleotide sequence of nucleotides 58 to 1081 of SEQ ID NO: 1, (ii) the cDNA sequence contained in the partial nucleotide sequence of nucleotides 58 to 1081 of SEQ ID NO: 1, or (iii) a full-length complementary strand of 0) or (ii); or allelic variants and subsequences thereof (Sambrook et al., 1989, supra), as defined herein. In a preferred aspect, the complementary strand comprises the full-length complementary strand of the partial nucleotide sequence of nucleotides 58 to 1081 of SEQ ID NO: 1.

The present invention also relates to an isolated polynucleotide comprising a nucleotide sequence comprising a partial nucleotide sequence obtained by (a) hybridizing a population of DNA under very low, low, medium, medium-high, high, or very high stringency conditions with (i) the partial nucleotide sequence of nucleotides 58 to 1081 of SEQ ID NO: 1, (ii) the cDNA sequence contained in the partial nucleotide sequence of nucleotides 58 to 1081 of SEQ ID NO: 1, or (iii) a full-length complementary strand of (i) or (ii); and (b) isolating the hybridizing polynucleotide, which encodes a polypeptide having beta-glucosidase activity.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotides sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* esparto proteinase, *Aspergillus niger* neutral alpha-amylase, *Aspergillus niger* acid stable alpha-amylase, *Aspergillus niger* or *Aspergillus awamori* glucoamylase (glaA) *Rhizomucor miehei* lipase, *Aspergillus oryzae* alkaline protease, *Aspergillus oryzae* triose phosphate isomerase, *Aspergillus nidulans* acetamidase, *Fusariurn venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* those phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that encodes a signal peptide linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence, Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin. *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems in yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3. LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), SC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67: Cullen et al., 1987, *Nucleic Acids Research* 15: 9163-9175: WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides having beta-glucosidase activity. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium, Gram positive bacteria include, but not limited to, *Bacillus*, *Streptococcus*, *Streptomyces*, *Staphylococcus*, *Enterococcus*, *Lactobacillus*, *Lactococcus*, *Clostridium*, *Geobacillus*, and *Oceanobacillus*. Gram negative bacteria include, but not limited to, *E. coli*, *Pseudomonas*, *Salmonella*, *Campylobacter*, *Helicobacter*, *Flavobacterium*, *Fusobacterium*, *Hyobacter*, *Neisseria*, and *Ureaplasma*.

The bacterial host cell may be any *Bacillus* cell. *Bacillus* cells useful in the practice of the present invention include, but are not limited to, *Bacillus alkalophifus*, *Bacillus amyloliquefaciens*, *Bacillus brevis*, *Bacillus circulans*, *Bacillus clausil*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus Bacillus subtilis*, and *Bacillus thuringiensis* cells.

In a preferred aspect, the bacterial host cell is a *Bacillus amyloliquefaciens*, *Bacillus lentus*, *Bacillus licheniformis*, *Bacillus steamthermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis*, *Streptococcus pyogenes*, *Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coeficolor, Streptomyces griseus*, and *Streptomyces lividens* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et at, 1988, *Nucleic Acids Res*, 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol*, 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbial.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Joilick, 1991, *Microbios.* 68: 189-207, by electroporation (see, e.g., Buckley at al., 1999, *Appl. Environ. Microbiol.* 65: 3800-3804) or by conjugation (see, e.g., Clewell, 1981, *Microbial. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell, "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et at., 1995, supra).

In a more preferred aspect, the fungal host cell is a yeast cell. "Yeast" as used herein includes ascosporogenous yeast (Endomycetales), basidiosporogenous yeast, and yeast belonging to the Fungi imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces dougfasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleuratus, Schizophytlum, Talaromyces, Thermoascus, Thiefavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookweilense, Fusarium culmorum, Fusarium graminearum, Fusarium graminutn, Fusarium heterosporum, Fusarium negundi, Fusarium oxysporum, Fusarium reticulatum, Fusariurn roseum, Fusarium sambucinum, Fusarium sarcochrown, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermisoora, Chrysosporium keratinophilum, Chrysosporium lucknowense, Chrysosporium tropicum, Chrysosporium merdarium, Chrysosporium inops, Chrysosporium pannicola, Chrysosporium queensiandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiate, Pleurotus eryngii, Thielavia terrestris, Trametes villosa, Trametes versicolor, Trichoderma harzianum, Trichoderma koningii, Trichoderma ionaibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier at al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Penicillium*. In a more preferred aspect, the cell is *Penicillium brasilianum*. In a most preferred aspect, the cell is *Penicillium brasilianum* IBT 20888.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant polynucleotide comprising a nucleotide sequence comprising at least one mutation in the partial nucleotide sequence of nucleotides 58 to 1081 of SEQ ID NO: 1, wherein the mutant polynucleotide encodes a polypeptide comprising an amino acid sequence comprising the partial amino acid sequence of amino acids 20 to 267 of SEQ ID NO: 2; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having baeta-glucosidase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidapsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck at al., 1980, *Cell* 21: 285-294, Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et at., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen at al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka at al., 1993, *Plant Physiology* 102: 991-1000, the chlorella virus adenine methyltransferase gene promoter (Mitre and Higgins, 1994, *Plant Molecular Biology* 26: 85-93), or the aldP gene promoter from rice (Kagaya at al, 1995, *Molecular and General Genetics* 248, 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu at al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535: Shimamoto at al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281: Shimamoto, 1994, *Current Opinion Biotechnology* 5: 158-162: Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, cotransformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having beta-glucosidase activity of the present invention under conditions conducive for production of the polypeptide; and (b) recovering the polypeptide.

Removal or Reduction of Beta-Glucosidase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA, sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide, comprising; (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of beta-glucosidase activity by fermentation of a cell that produces both a polypeptide of the present invention as well as the protein product of interest by adding an effective amount of an agent capable of inhibiting beta-glucosidase activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of beta-glucosidase activity by cultivating the cell under conditions permitting the expression of the product, subjecting the resultant culture broth to a combined pH and temperature treatment so as to reduce the beta-glucosidase activity substantially, and recovering the product from the culture broth. Alternatively, the combined pH and temperature treatment may be performed on an enzyme preparation recovered from the culture broth. The combined pH and temperature treatment may optionally be used in combination with a treatment with an beta-glucosidase inhibitor.

In accordance with this aspect of the invention, it is possible to remove at least 60%, preferably at least 75%, more preferably at least 85%, still more preferably at least 95%, and most preferably at least 99% of the beta-glucosidase activity. Complete removal of beta-glucosidase activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially beta-glucosidase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulolytic enzyme, oxidoreductase, or plant cell-wall degrading enzyme. Examples of such enzymes include an aminopeptidase, amylase, amyloglucosidase, carbohydrase, carboxypeptidase. catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The beta-glucosidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from beta-glucosidase activity that is produced by a method of the present invention.

Methods of Inhibiting Expression of a Polypeptide Having Beta-Glucosidase Activity The present invention also relates to methods of inhibiting the expression of a polypeptide having beta-glucosidase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the partial nucleotide sequence of nucleotides 58 to 1081 of SEQ ID NO: 1 for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing therapeutics. In one aspect, the invention provides methods to selectively degrade RNA using the dsRNAis of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. No. 6,506,559: U.S. Pat. No. 6,511,824; U.S. Pat. No. 6,515,109, and U.S. Pat. No. 6,489,127.

Compositions

The present invention also relates to compositions comprising a polypeptide of the present invention. Preferably, the compositions are enriched in such a polypeptide. The term "enriched" indicates that the beta-glucosidase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusariurn negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Processing of Cellulosic Material

The present invention also relates to methods for degrading or converting a cellulosic material, comprising: treating the cellulosic material with a cellulolytic enzyme composition in the presence of a polypeptide having beta-glucosidase activity of the present invention in a preferred aspect, the method further comprises recovering the degraded or converted cellulosic material.

The present invention also relates to methods of producing a fermentation product, comprising: (a) saccharifying a cellulosic material with a cellulolytic enzyme composition in the presence of a polypeptide having beta-glucosidase activity of the present invention; (b) fermenting the saccharified cellulosic material of step (a) with one or more fermenting microorganisms to produce the fermentation product; and (c) recovering the fermentation product from the fermentation.

The present invention also relates to methods of fermenting a cellulosic material, comprising: fermenting the cellulosic material with one or more fermenting microorganisms, wherein the cellulosic material is saccharified with a cellulolytic enzyme composition in the presence of a polypeptide having beta-glucosidase activity of the present invention and the presence of the polypeptide having beta-glucosidase activity increases the degradation of the cellulosic material compared to the absence of the polypeptide having beta-glucosidase activity. In a preferred aspect, the fermenting of the cellulosic material produces a fermentation product. In another preferred aspect, the method further comprises recovering the fermentation product from the fermentation.

The composition and the polypeptide having beta-glucosidase activity can be in the form of a crude fermentation broth with or without the cells removed or in the form of a semi-purified or purified enzyme preparation or the composition can comprise a host cell of the present invention as a source of the polypeptide having beta-glucosidase activity in a fermentation process with the biomass.

The methods of the present invention can be used to saccharify a cellulosic material to fermentable sugars and convert the fermentable sugars to many useful substances, e.g., chemicals and fuels. The production of a desired fermentation product from cellulosic material typically involves pretreatment, enzymatic hydrolysis (sacchanfication), and fermentation.

The processing of cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultanoeus, include, but are not limited to, separate hydrolysis and fermentation (SHF); simultaneous saccharification and fermentation (SSF); simultaneous saccharification and cofermentation (SSCF); hybrid hydrolysis and fermentation (HHF); SHCF (separate hydrolysis and co-fermentation), HHCF (hybrid hydrolysis and fermentation), and direct microbial conversion (DMC). SHF uses separate process steps to first enzymatically hydrolyze lignocellulose to fermentable sugars, e.g, glucose, cellobiose, cellotriose, and pentose sugars, and then ferment the fermentable sugars to ethanol. In SSF, the enzymatic hydrolysis of lignocellulose and the fermentation of sugars to ethanol are combined in one step (Philipidis, G. P., 1996, Cellulose bioconversion technology, in *Handbook on Bioethanol: Production and Utilization*, Wyman, C. E. ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis separate step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, lignocellulose hydrolysis, and fermentation) in one or more steps where the same organism is used to produce the enzymes for conversion of the lignocellulose to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38: Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu. S. K., and Lee. J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn. A. P., Davydkin, I. Y., Davydkin, V. Y., Prates, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: Fluidized bed, upflow blanket, immobilized, and extruder type reactors for hydrolysis and/or fermentation.

Pretreatment.

In practicing the methods of the present invention, any pretreatment process known in the art can be used to disrupt plant cell wall components. The cellulosic material can also be subjected to pre-soaking, wetting, or conditioning prior to pretreatment using methods known in the art. Conventional pretreatments include, but are not limited to, steam pretreatment (with or without explosion), dilute acid pretreatment, hot water pretreatment, lime pretreatment, wet oxidation, wet explosion, ammonia fiber explosion, organosolv pretreatment, and biological pretreatment. Additional pretreatments include ultrasound, electroporation, microwave, supercritical $CO_2$, supercritical $H_2O$, and ammonia percolation.

The cellulosic material can be pretreated before hydrolysis and/or fermentation. Pretreatment is preferably performed prior to the hydrolysis. Alternatively, the pretreatment can be carried out simultaneously with hydrolysis, such as simultaneously with treatment of the cellulosic material with one or more cellulolytic enzymes, or other enzyme activities, to release fermentable sugars, such as glucose and/or maltose. In most cases the pretreatment step itself results in some conversion of biomass to fermentable sugars (even in absence of enzymes).

Steam Pretreatment. In steam pretreatment, the cellulosic material is heated to disrupt plant cell wall components, including lignin, hemicellulose, and cellulose to make the cellulose and other fractions, e.g., hemicellulase, accessible to enzymes. The lignocellulose material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol,* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-636). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotectnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures, such as 90-100° C., and high pressure, such as 17-20 bar, for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121:1133-1141; Teymouri et al., 2005, *Bioresource Technol* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et at., 2006, *Biotechnol. Bioeng.* 94: 851-861; Kurabi et al., 2005, *Appl. Biochem. Biotechnol.* 121:219-230). Sulphuric acid is usually added as a catalyst. In organosolv pretreatment, the majority of the hemicellulose is removed.

Other examples of suitable pretreatment methods are described by Schell at al., 2003, *Appl. Biochem. and Biotechnol.* Vol. 105-108, p. 69-85, and Mosier at al. 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. The acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with the cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, the cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: The cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, the cellulosic material is subjected to mechanical, chemical, or physical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol*, 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal. 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the pretreated cellulosic material is hydrolyzed to break down cellulose and alternatively also hemicellulose to fermentable sugars, such as glucose, xylose, xylulose, arabinose, maltose, mannose, galactose, or soluble oligosaccharides. The hydrolysis is performed enzymatically by a cellulolytic enzyme composition in the presence of a polypeptide having beta-glucosidase activity of the present invention. One or more of the enzymes of the composition can also be added sequentially.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulosic material (substrate) is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

In addition to a polypeptide having beta-glucosidase activity of the present invention, the cellulolytic enzyme composition may comprise any protein involved in the processing of a cellulose-containing material to glucose, and/or hemicellulose to xylose, mannose, galactose, and arabinose, their polymers, or products derived from them as described below. In one aspect, the cellulolytic enzyme composition comprises one or more enzymes selected from the group consisting of a cellulase, an endoglucanase, a cellobiohydrolase, and a beta-glucosidase. In another aspect, the cellulolytic enzyme composition further or even further comprises a polypeptide having cellulolytic enhancing activity. See, for example, WO 2005/074647, WO 2005/074656, and WO 2007/089290. In another aspect, the cellulolytic enzyme composition further or even further comprises one or more additional enzyme activities to improve the degradation of the cellulose-containing material. Preferred additional enzymes are hemicellulases, esterases (e.g., lipases, phospholipases, and/or cutinases), proteases, laccases, peroxidases, or mixtures thereof.

The enzymes can be derived or obtained from any suitable origin, including, bacterial, fungal, yeast, plant, or mammalian origin. The term "obtained" means herein that the enzyme may have been isolated from an organism that naturally produces the enzyme as a native enzyme. The term "obtained" also means herein that the enzyme may have been produced recombinantly in a host organism employing methods described herein, wherein the recombinantly produced enzyme is either native or foreign to the host organism or has a modified amino acid sequence, e.g., having one or more amino acids that are deleted, inserted and/or substituted. i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The cellulolytic enzyme composition may be a monocomponent preparation, e.g., an encloglucanase, a multicomponent preparation, e.g., endoglucanase(s), cellobiohydrolase(s), and beta-glucosidase(s), or a combination of multicomponent and monocomponent protein preparations. The cellulolytic proteins may have activity, i.e., hydrolyze the cellulose-containing material, either in the acid, neutral, or alkaline pH-range. One or more components of the cellulolytic enzyme composition may be a recombinant component, i.e., produced by cloning of a DNA sequence encoding the single component and subsequent cell transformed with the DNA sequence and expressed in a host (see, for example. WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

The enzymes used in the present invention can be in any form suitable for use in the methods described herein, such as a crude fermentation broth with or without cells or substantially pure polypeptides. The enzyme(s) can be a dry powder or granulate, a non-dusting granulate, a liquid, a stabilized liquid, or a protected enzyme(s). Liquid enzyme preparations can, for instance, be stabilized by adding stabilizers such as a sugar, a sugar alcohol or another polyol, and/or lactic acid or another organic acid according to established process. Protected enzymes can be prepared according to the process disclosed in EP 238,216.

Examples of commercial cellulolytic protein preparations suitable for use in the present invention include, for example, CELLUCLAST™ (available from Novozymes A/S) and NOVOZYM™ 188 (available from Novozymes A/S). Other commercially available preparations comprising cellulase that may be used include CELLUZYME™, CEREFLO™ and ULTRAFLO™ (Novozymes A/S). LAMINEX™ and SPEZYME™ CP (Genencor Int.), ROHAMENT™ 7069 W (Röhm GmbH), and FIBREZYME® LDI, FIBREZYME® LBR, or VISCOSTAR® 150L (Dyadic International, Inc., Jupiter, Fla., USA). The cellulase enzymes are added in amounts effective from about 0.001% to about 5.0% wt of solids, more preferably from about 0.025% to about 4.0% wt. of solids, and most preferably from about 0.005% to about 2.0% wt. of solids.

Examples of bacterial endoglucanases that can be used in the methods of the present invention, include, but are not limited to, an *Acidothermus celluiolyticus* endoglucanase (WO 91/05039; WO 93/15186; U.S. Pat. No. 5,275,944; WO 96/02551; U.S. Pat. No. 5,536,655. WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the methods of the present invention, include, but are not limited to, a *Trichoderma reesei* endoglucanase (Penttila at al, 1986, *Gene* 45: 253-263; GENBANK™ accession no. M15665); *Trichoderma reesei* endoglucanase II (Saloheimo, et al., 1988, Gene 63:11-22; GENBANK™ accession no. M19373); *Trichoderma reesei* endoglucanase III (Okada et al., 1988, *Appl. Environ. Microbiol.* 64: 555-563; GEN- BANK™ accession no. AB003694); *Trichodenna reesei* endoglucanase IV (Saloheimo et al., 1997, *Eur. J. Biochem.* 249: 584-591; GENBANK™ accession no. Y11113); and *Trichoderma reesei* endoglucanase V (Saloheimo at al., 1994, *Molecular Microbiology* 13: 219-228; GENBANK™ accession no. Z33381); *Aspergillus aculeatus* endoglucanase (Ooi et al., 1990, *Nucleic Acids Research* 18: 5884); *Aspergillus kawachii* endoglucanase (Sakamoto at al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V; *Myceliophthora thermophila* CBS 117.65 endoglucanase; basidiomycete CBS 495.95 endoglucanase; basidiomycete CBS 494.95 endoglucanase; *Thielavia terrestris* NRRL 8126 CEL6B endoglucanase; *Thielavia terrestris* NRRL 8126 CEL6C endoglucanase); *Thielavia terrestris* NRRL 8126 CEL7C endoglucanase; *Thielavia terrestris* NRRL 8126 CEL7E endoglucanase; *Thielavia terrestris* NRRL 8126 CEL7F endoglucanase; *Cladorrhinum foecundissimum* ATCC 62373 CEL7A endoglucanase; and *Trichoderma reesei* strain No. VTT-D-80133 endoglucanase (GENBANK™ accession no. M15665).

Examples of cellobiohydrolases useful in the methods of the present invention include, but are not limited to, *Trichoderma reesei* cellobiohydrolase I; *Trichoderma reesei* cellobiohydrolase II; *Humicola insoiens* cellobiohydrolase I, *Mycellophthora thermophile* cellobiohydrolase II, *Thielavia terrestris* cellobiohydrolase II (CEL6A), *Chaetomium thermophilum* celloblohydrolase I, and *Chaetotnium thenrophilum* cellobiohydrolase II.

Examples of beta-glucosidases useful in the methods of the present invention include, but are not limited to, *Aspergillus oryzae* beta-glucosidase; *Aspergillus fumigatus* beta-glucosidase; *Penicillium brasilianum* IBT 20888 beta-glucosidase; *Aspergillus niger* beta-glucosidase; and *Aspergilius aculeatus* beta-glucosidase.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499. The *Penicillium brasilianum* polypeptide having beta-glucosidase activity can be obtained according to WO 2007/019442. The Aspergillus niger polypeptide having beta-glucosidase activity can be obtained according to Dan et al., 2000, *J. Biol. Chem.* 275: 4973-4980. The *Aspergillus aculeatus* polypeptide having beta-glucosidase activity can be obtained according to Kawaguchi et al., 1996, *Gene* 173: 287-288.

The beta-glucosidase may be a fusion protein. In one aspect, the beta-glucosidase is the *Aspergillus oryzae* beta-glucosidase variant BG fusion protein or the *Aspergillus oryzae* beta-glucosidase fusion protein obtained according to WO 2008/057637.

Other endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Brochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in EP 495,257, EP 531,315, EP 531, 372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/0076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 4,435,307, U.S. Pat. No. 5,457,046, U.S. Pat. No. 5,648,263, U.S. Pat. No. 5,686,593, U.S. Pat. No. 5,691,178, U.S. Pat. No. 5,763,254, and U.S. Pat. No. 5,776,757.

In the methods of the present invention, any polypeptide having cellulolytic enhancing activity can be used.

In a first aspect, the polypeptide having cellulolytic enhancing activity comprises the following motifs:

[ILMV]-P-X(4,5)-G-X-Y-[ILMV]-X-R-X-[EQ]-X(4)-

[HNQ] and [FW]-[TF]-K-[AIV], wherein X is any amino acid, X(4,5) is any amino acid at 4 or 5 contiguous positions, and X(4) is any amino acid at 4 contiguous positions.

The polypeptide comprising the above-noted motifs may further comprise:

H-X(1,2)-G-P-X(3)-[YW]-[AILMV],

[EQ]-X-Y-X(2)-C-X-[EHQN]-[FILV]-X-[ILV],
or

H-X(1,2)-G-P-X(3)-[YW]-[AILMV] and [EQ]-X-Y-X(2)-C-X-[EHQN]-[FILV]-X-[ILV], wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred aspect, the polypeptide having cellulolytic enhancing activity further comprises H-X(1,2)-G-P-X(3)-[YW]-[AILMV]. In another preferred aspect, the isolated polypeptide having cellulolytic enhancing activity further comprises [EQ]-X-Y-X(2)-C-X-[EHQN]-[FILV]-X-[ILV]. In another preferred aspect, the polypeptide having cellulolytic enhancing activity further comprises H-X(1,2)-G-P-X(3)-[YW]-[AILMV] and [EQ]-X-Y-X(2)-C-X-[EHQN]-[FILV]-X-[ILV].

In a second aspect, the polypeptide having cellulolytic enhancing activity comprises the following motif:

[ILMV]-P-x(4,5)-G-x-Y[ILMV]-x-R-x-[EQ]-x(3)-A-

[HNQ], wherein x is any amino acid, x(4,5) is any amino acid at 4 or 5 contiguous positions, and x(3) is any amino acid at 3 contiguous positions. In the above motif, the accepted IUPAC single letter amino acid abbreviation is employed.

Examples of polypeptides having cellulolytic enhancing activity useful in the methods of the present invention include, but are not limited to, polypeptides having cellulolytic enhancing activity from *Thielavia terrestris* (WO 2005/074647); polypeptides having cellulolytic enhancing activity from *Thermoascus aurantiacus* (WO 2005/074656); and polypeptides having cellulolytic enhancing activity from *Trichoderma reesei*, (WO 2007/089290).

The cellulolytic enzymes and proteins used in the methods of the present invention may be produced by fermentation of the above-noted microbial strains on a nutrient medium containing suitable carbon and nitrogen sources and inorganic salts, using procedures known in the art (see, e.g., Bennett. J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and cellulolytic enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of a cellulolytic enzyme. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the cellulolytic enzyme to be expressed or isolated. The resulting cellulolytic enzymes produced by the methods described above may be recovered from the fermentation medium and purified by conventional procedures.

The optimum amounts of the enzymes and polypeptides having beta-glucosidase activity depend on several factors including, but not limited to, the mixture of component cellulolytic enzymes, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, an effective amount of cellulolytic enzyme(s) to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another preferred aspect, an effective amount of a polypeptide having beta-glucosidase activity to cellulosic material is about 0.01 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another preferred aspect, an effective amount of polypeptide(s) having beta-glucosidase activity to cellulolytic enzyme(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic enzyme(s).

Fermentation.

The fermentable sugars obtained from the pretreated and hydrolyzed cellulosic material can be fermented by one or more fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous. Such methods include, but are not limited to, separate hydrolysis and fermentation (SHF); simultaneous saccharification and fermentation (SSF); simultaneous saccharification and cofermentation (SSCF); hybrid hydrolysis and fermentation (HHF); SHCF (separate hydrolysis and co-fermentation), HHCF (hybrid hydrolysis and fermentation), and direct microbial conversion (DMC).

Any suitable hydrolyzed cellulosic material can be used in the fermentation step in practicing the present invention. The material is generally selected based on the desired fermentation product, the substance to be obtained from the fermentation, and the process employed, as is well known in the art. Examples of substrates suitable for use in the methods of present invention, include cellulosic materials, such as wood or plant residues or low molecular sugars DP1-3 obtained from processed cellulosic material that can be metabolized by the fermenting microorganism, and which can be supplied by direct addition to the fermentation medium.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_6$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin of al., 2006, *Appl. Microbiol. Biotechnol.* 69: 627-642.

Examples of fermenting microorganisms that can ferment C6 sugars include bacterial and fungal organisms, such as yeast. Preferred yeast includes strains of the *Saccharomyces* spp., preferably *Saccharomyces cerevisiae*.

Examples of fermenting organisms that can ferment C5 sugars include bacterial and fungal organisms, such as yeast. Preferred C5 fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis: Hansenula*, such as *Hansenula anomala; Klyveromyces*, such as *K. fragilis*; *Schizosaccharomyces*, such as *S. pombe*; and *E. coli*., especially *E. coli* strains that have been genetically modified to improve the yield of ethanol.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyverornyces fragills*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pechysalen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermacellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIO™ (available from DSM Specialties).

In a preferred aspect, the fermenting microorganism has been genetically modified to provide the ability to ferment pentose sugars, such as xylose arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbial.* 64: 1852-1859: Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbial.* 61: 4184-4190: Kuyper at al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram at al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomenas mobilis* strain by metabolic pathway engineering, *Appl. Environ. Microbiol.* 62: 4465-4470).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded lignocellulose or hydrolysate and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some, e.g., bacterial fermenting organisms have higher fermentation temperature optima. Yeast or another microorganism is preferably applied in amounts of approximately 10 to $10^{12}$, preferably from approximately $10^7$ to $10^{10}$, especially approximately $2 \times 10^6$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example. Alfenore et at improving ethanol production and viability of Saccharomyces cerevisiae by a vitamin feeding strategy during fed-batch process. Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, butanoi, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid): a ketone (e.g., acetone); an amino acid (e.g., aspartic acid, glutamic acid, glycine, lysine, serine, and threonine); and a gas (e g., methane hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong. C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002. The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji. T. C Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example. Richard. A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997. Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol.% can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 19 of SEQ ID NO: 2. The present invention also relates to nucleic acid constructs comprising a gene encoding a protein, wherein the gene is operably linked to the polynucleotide encoding the signal peptide comprising or consisting of amino acids 1 to 19 of SEQ ID NO: 2, wherein the gene is foreign to the polynucleotide.

In a preferred aspect, the nucleotide sequence of the polynucleotide comprises or consists of nucleotides 1 to 57 of SEQ ID NO: 1.

The present invention also relates to recombinant expression vectors and recombinant host cells comprising such nucleic acid constructs.

The present invention also relates to methods of producing a protein comprising (a) cultivating such a recombinant host cell under conditions suitable for production of the protein: and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides that comprise a combination of partial or complete polypeptide sequences obtained from at least two different proteins wherein one or more (several) may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

DNA Sequencing

DNA sequencing was performed using an Applied Biosystems Model 3130X Genetic Analyzer (Applied Biosystems, Foster City, Calif., USA) using dye terminator chemistry (Giesecke et al., 1992, *Journal of Virol. Methods* 38: 47-60). Sequences were assembled using phred/phrap/consed (University of Washington, Seattle, Wash., USA) with sequence specific primers.

Strains

*Penicillium brasilianum* strain IBT 20888 (IBT Culture Collection of Fungi, Technical University of Denmark, Copenhagen, Denmark) was used as the source of beta-glucosidase.

Media and Solutions

TE was composed of 10 mM Tris-1 mM EDTA.

LB medium was composed per liter of 10 g of tryptone. 5 g of yeast extract, and 5 g of sodium chloride.

LB plates were composed per her of 10 g of tryptone, 5 g of yeast extract. 5 g of sodium chloride, and 15 g of Bacto Agar.

STC was composed of 1.2 M sorbitol, 10 mM Tris-HCl, and 10 mM $CaCl_2$, pH 7.5.

PEG solution was composed of 60% PEG 4000, 10 mM Tris-HCl, and 10 mM $CaCl_2$, pH 7.5.

YPM medium was composed per liter of 10 g of yeast extract, 20 g of peptone, and 2% maltose.

Example 1

Isolation of Genomic DNA from *Penicillium brasilianum*

Spores of *Penicillium brasilianum* strain IBT 20888 were propagated on rice according to Carlsen, 1994, Ph.D. thesis. Department of Biotechnology, The Technical University of Denmark. The spores were recovered with 20 ml of 0.1% TWEEN® 20 and inoculated at a concentration of $1 \times 10^6$ spores per ml into 100 ml of Mandels and Weber medium (Mandels and Weber, 1969, *Adv. Chem. Ser.* 95: 394-414) containing 1% glucose supplemented per liter with 0.25 g of yeast extract and 0.75 g of Bactopeptone in a 500 ml baffled shake flask. The fungal mycelia were harvested after 24 hours of aerobic growth at 30° C., 150 rpm.

Mycelia were collected by filtration through a NALGENE® DS0281-5000 filter (Naige Nunc International Corporation, Rochester, N.Y., USA) until dryness and frozen in liquid nitrogen. The frozen mycelia were ground to a powder in a dry ice chilled mortar and distributed to a screw-cap tube. The powder was suspended in a total volume of 40 ml of 50 mM CAPS (3-(cyclohexylamino)-1-propanesulfonic acid)-NaOH pH 11 buffer containing 0.5% lithium dodecyl sulfate and 0.5 mM EDTA. The suspension was placed at 60° C. for 2 hours and periodically resuspended by inversion. To the suspension was added an equal volume of phenol:chloroform (1:1 v/v) neutralized with 0.1 M Tris base, and the tube was mixed on a rotating wheel at 37° C. for 2 hours. After centrifugation at 2500 rpm for 10 minutes in a Sorvall H1000B rotor, the aqueous phase (top phase) was re-extracted again with phenol:chloroform (1:1 v/v) and centrifuged at 15,000×g for 5 minutes. The aqueous phase from the second extraction was brought to 2.5 M ammonium acetate (stock 10 M) and placed at −20° C. until frozen. After thawing, the extract was centrifuged at 15,000×g for 20 minutes in a cold rotor. The pellet (primarily rRNA) was discarded and the nucleic acids in the supernatant were precipitated by addition of 0.7 volumes of isopropanol. After centrifugation at 15,000×g for 15 minutes, the pellet was rinsed three times with 5 ml of 70% ethanol (without resuspension), air-dried almost completely, and dissolved in 1.0 ml of 0.1×TE. The dissolved pellet was transferred to two 1.5 ml microfuges tubes. The nucleic acids were precipitated by addition of ammonium acetate (0.125 ml) to 2.0 M and ethanol to 63% (1.07 ml) and centrifuged at maximum speed for 10 minutes in a Sorvall MC 12V microcentrifuge (Kendra Laboratory Products, Asheville, N.C., USA). The pellet was rinsed twice with 70% ethanol, air-dried completely, and dissolved in 500 μl of 0.1×TE.

Example 2

Preparation of a Genomic DNA Library

Genomic libraries were constructed using a TOPO® Shotgun Subcloning Kit (Invitrogen, Carlsbad, Calif., USA). Briefly, total cellular DNA was sheared by nebulization under 10 psi nitrogen for 15 seconds and size-fractionated on 1% agarose gels using 40 mM Tris base-20 mM sodium acetate-1 mM disodium EDTA (TAE) buffer. DNA fragments migrating in the size range 3-6 kb were excised and eluted using a MINIELUTE™ Gel Extraction Kit (QIAGEN Inc, Valencia, Calif., USA). The eluted fragments were size-fractionated again using a 1% agarose gel as above and DNA fragments migrating in the size range 3-6 kb were excised and eluted using a MINIELUTE™ Gel Extraction Kit.

The eluted DNA fragments were blunt end repaired and dephosphorylated using shrimp alkaline phosphatase (Roche Applied Science, Manheim, Germany). The blunt end DNA fragments were cloned into a pCR4Blunt-TOPO® vector (Invitrogen, Carlsbad, Calif., USA) according to the manufacturer's instructions, transformed into electrocompetent *E. coli* TOP10 cells by electroporation, and plated on LB plates supplemented with 100 µg of ampicillin per ml. The electroporation resulted in 15,300 clones.

Example 3

Purification of *Penicillium brasilianum* Beta-Glucosidase

*Penicillium brasilianum* strain IBT 20888 was grown in 4 liters of Mandeis and Weber medium (Mandels and Weber, 1969, supra) in a 5 liter bioreactor supplemented per liter with 1 g of yeast extract, 3 g of bactopeptone, 30 g of cellulose, and 10 g of xylan. Spores were propagated on rice according to Carlsen, 1994, supra. The bioreactor was inoculated at a concentration of $1 \times 10^6$ spores per ml. The pH was maintained at 5.0 by addition of either 2 M $NH_4OH$ or 2 M HCl. The temperature was maintained at 30° C. The aeration was 4 liters per minute and 300-500 rpm. After 111 hours, the cultivation was terminated and the broth was filtered through a glass fiber filter (GD 120, Advantec, Japan).

Beta-glucosidase activity was measured at room temperature in 50 mM sodium citrate pH 4.8. The substrate was 1 mM 4-nitrophenyl-beta-D-glucopyranoside in 50 mM sodium citrate pH 4.8. The beta-glucosidase hydrolyzes the agliconic bond between 4-nitrophenol and glucose. The liberated 4-nitrophenol is yellow in alkaline solution and can be determined spectrophotometrically at 405 nm. One international unit of activity (U) is defined as the amount of enzyme liberating 1 µmole of 4-nitrophenol per minute at pH 4.8, 25° C.

Protein concentration was determined by SDS-PAGE. Fifteen µl of sample was added to 15 µl of SDS-PAGE sample buffer (1.17 M sucrose, 1 M Tris-HCl, pH 8.5, 278 mM SDS, 2.05 mM EDTA, 0.88 mM Brilliant Blue G, and 0.2 M dithiothreitol) in an EPPENDORF® tube and heated to 70° C. for 10 minutes. Following heating the diluted sample was applied to a precast 4-12% Bis-Tris pre-cast gel (Invitrogen, Groningen, The Netherlands). In addition, a MARK12™ protein standard mixture (Invitrogen, Carlsbad, Calif., USA) was applied to the gel.

The gel was run in an Xcell SURELOCK™ gel apparatus (Invitrogen, Carlsbad, Calif., USA) for 50 minutes at 200 V. The running buffer was made by a 20-fold dilution of the standard buffer (1 M MOPS, 1 M TRIS, and 1% SDS). A 0.5 ml volume of NuPAGE® Antioxidant (Invitrogen, Carlsbad, Calif., USA) was added to the upper (cathode) buffer chamber. Following electrophoresis the gel was incubated for 60 minutes in a staining solution consisting of 0.1% (w/v) Coomassie Brilliant Blue R-250 dissolved in 10% acetic acid, 40% methanol, and 50% $H_2O$. Destaining of the gel was performed in 10% acetic acid, 30% methanol, and 60% $H_2O$.

Before purification, the filtrate was concentrated and buffer exchanged to 20 mM triethanolamine (TEA)-HCl pH 7.5 using an ultrafiltration unit equipped with a PM10 membrane with 10 kDa cut-off (Millipore, Bedford, Mass., USA). The enzyme purification was performed at room temperature using a FPLC system (Amersham Bioscience, Uppsala, Sweden). Between each purification step, the buffer was exchanged in the pooled fractions to the sample buffer using either an Amicon ultrafiltration unit or a 3.5 ml MICROSEP® ultrafiltration unit with a 10 kDa cut-off (Pall Life Sciences, Ann Arbor, Mich., USA). Elution of the beta-glucosidase was monitored at 280 nm.

The retentate (38.5 ml) was loaded onto a XK 26 column packed with 75 ml of Q SEPHAROSE® HP (Amersham Bioscience, Uppsala, Sweden). The column was washed with 180 ml of sample buffer. The sample buffer was 20 mM TEA-HCl pH 7.5. The enzyme was eluted with a gradient up to 50% (over 800 ml) of 20 mM TEA-HCl pH 7.5 with 1 M NaCl. Fractions of 10 ml were collected, assayed for beta-glucosidase activity, and fractions 81 to 85 were pooled.

The retentate (2.0 ml) from the previous step was loaded onto a SEPHAROSE® 75 10/300 GL column (Amersham Bioscience, Uppsala, Sweden) using 100 mM $NaCH_3CO_2$ pH 4.8 with 200 mM NaCl as the sample buffer. The enzyme was eluted with 60 ml of the same buffer. Fractions of 2 ml were collected, assayed for beta-glucosidase activity, and fractions 6 to 9 were pooled based on activity and purity (SDS-PAGE).

The retentate (14 ml) from the SUPERDEX® 75 step was loaded onto a 6 ml RESOURCE® Q column (Amersham Bioscience, Uppsala, Sweden) using 10 mM $NaCH_3CO_2$ pH 4.8 as the sample buffer. The column was washed with 30 ml of sample buffer. The enzyme was eluted with a gradient up to 50% (over 180 ml) of 500 mM $NaCH_3CO_2$ pH 4.8, Fractions of 2 ml were collected, assayed far beta-glucosidase activity, and fraction 75 was chosen for N-terminal sequencing based on activity and appearing relatively pure by SDS-PAGE.

Example 4

N-Terminal Sequencing

A 100 µl aliquot of purified *Penicillium brasilianum* beta-glucosidase (Example 3) was added to 100 µl of SDS-PAGE sample buffer (4 ml of 0.5 M Tris-HCl pH 6.8, 20 ml of 10% SDS, 20 ml of glycerol (87%), 56 ml of MILLI-Q® filtered $H_2O$, and 15 grains of bran phenol blue) in an EPPENDORF® tube and heated to 95° C. for 4 minutes. Following heating four 20 µl aliquots of the diluted sample were applied separately to a precast 4-20% SDS polyacrylamide gel (Invitrogen. Carlsbad, Calif., USA). In addition to the four Lanes containing the sample, a MARK12® protein standard mixture was applied to the gel.

The gel was run in an Xcell SURELOCK™ gel apparatus for 90 minutes with initial power settings of 40 mA at maximum 135 V. Following electrophoresis the gel was incubated for 5 minutes in a blotting solution consisting of 10 mM CAPS pH 11 containing 6% methanol. A PROBLOTT® membrane (Applied Biosystems, Foster City, Calif., USA) was wetted for 1 minute in pure methanol before being placed in the blotting solution for 5 minutes in order to saturate the membrane with 10 mM CAPS pH 11 containing 6% methanol.

Electroblotting was carried out in a Semi Dry Blotter II apparatus (KemEnTec, Copenhagen, Denmark) as follows. Six pieces of Whatman no. 1 paper wetted in the blotting solution were placed on the positive electrode of the blotting apparatus followed by the ProBlott membrane, the polyacrylamide gel, and six pieces of Whatman no. 1 paper wetted in blotting solution. The blotting apparatus was assembled thereby putting the negative electrode in contact with the upper stack of Whatman no. 1 paper. A weight of 11.3 kg was placed on top of the blotting apparatus. The electroblotting was performed at a current of 175 mA for 180 minutes.

Following the electroblotting the PROBLOTT® membrane was stained for 1 minute in 0.1% (w/v) Coomassie Brilliant Blue R-250 dissolved in 60% methanol, 1% acetic acid, 39% $H_2O$. Destaining of the ProBlott membrane was performed in 40% aqueous methanol for 5 minutes before the membranes were rinsed in deionized water. Finally the PROBLOTT® membrane was air-dried.

For N-terminal amino acid sequencing two pieces of the PROBLOTT® membrane consisting of a 105 kDa band were cut out and placed in the blotting cartridge of an PROCISE® Protein Sequencer (Applied Biosystems, Foster City, Calif., USA). The N-terminal sequencing was carried out using the method run file for membrane samples (Pulsed liquid PVDF) according to the manufacturer's instructions.

The N-terminal amino acid sequence was deduced from the resulting chromatograms by comparing the retention time of the peaks in the chromatograms to the retention times of the PTH-amino-acids in the standard chromatogram.

The N-terminal amino acid sequence of the purified *Penicillium brasilianum* beta-glucosidase was determined directly using a PROCISE® 494 HT Sequencing System (Applied Biosystems, Foster City, Calif., USA). The N-terminal sequence was determined to be Lys-Asp-Leu-Ala-Tyr-Ser-Pro-Pro-Tyr-Tyr-Pro-Ser-Pro-Trp-Ala-Thr-Gly-Glu-Gly-Asp (amino acids 20 to 39 of SEQ ID NO: 2).

Example 5

PCR Amplifications

Based on the N-terminal amino acid sequence of the purified *Penicillium brasilianum* beta-glucosidase (Example 4), a forward primer was designed as shown below using the CODEHOP strategy (Rose et al., 1998, *Nucleic Acids Res.* 26: 1628-35). From database information on other beta-glucosidases, a reverse primer was designed as shown below using the CODEHOP strategy.

```
Forward primer:
                                       (SEQ ID NO: 3)
5'-TCTCCTCCTTACTACCCTTCTCCNTGGGCNAC-3'

Reverse primer:
                                       (SEQ ID NO: 4)
5'-GTCGGTCATGACGAAGCCNKGRAANCC-3'
where R = A or G, Y = C or T,
K = G or T and N = A, C, G or T
```

Amplification reactions (30 µl) were prepared using approximately 1 µg of *Penicillium brasilianum* genomic DNA as template. In addition, each reaction contained the following components: 30 pmol of the forward primer, 30 pmol of the reverse primer, 200 µM each of dATP, dCTP, dGTP, and dTTP, 1× AMPLITAQ® DNA polymerase buffer (Applied Biosystems, Foster City, Calif., USA), and 0.5 unit of AMPLITAQ® DNA polymerase (5.0 U/µl, Applied Biosystems, Foster City, Calif., USA). The reactions were incubated in a ROBOCYCLER® temperature cycler (Stratagene, La Jolla, Calif., USA) programmed for 1 cycle at 96° C. for 3 minutes and at 72° C. for 3 minutes; 34 cycles each at 95° C. for 0.5 minute, 56° C. for 0.5 minutes, and 72° C. for 1.5 minutes; 1 cycle at 72° C. for 7 minutes, and a soak cycle at 6° C. Taq polymerase was added at 72° C. in the first cycle.

PCR reaction products were separated on a 2% agarose gel (Amresco, Solon, Ohio, USA) using TAE buffer. A band of approximately 950 bp was excised from the gel and purified using a MINIELUTE™ Gel Extraction Kit (QIAGEN Inc., Valencia, Calif., USA) according to the manufacturer's instructions. The purified PCR product was subsequently cloned into a pCR2.1 TOPO® vector (Invitrogen, Carlsbad, Calif., USA) according to the manufacturers instructions to produce a vector designated pCR2.1GH3B (FIG. 2) and analyzed by DNA sequencing to confirm its identity as a partial sequence of a Family 3 glycosyl hydrolase.

Example 6

Screening of Genomic Library

Colony lifts were performed (Maniatis et al., 1982, *Molecular Cloning, A Laboratory Manual*, Cold Spring Harbor Press, Cold Spring Harbor, N.Y.) and the DNA was cross-linked onto HYBOND® N+ membranes (Amersham, Arlington Heights, Ill.) for 2 hours at 80° C. The membranes from the colony lifts were pre-wetted using 0.2×SSC (003 M NaCl, 0.003 M sodium citrate), 0.2% SDS. The pre-wetted filters were placed in a beaker with 7.5 ml of hybridization solution (6×SSPE [0.9 M NaCl, 0.06 M NaH$_2$PO$_4$, and 6 mM EDTA], 7% SDS) per filter at 68° C. in a shaking water bath for 0.5 hour. The subcloned product of the PCR amplification described in Example 5 was amplified from pCR2.1GH3A by PCR amplification using primers homologous to the vector, as shown below.

```
5'-CTTGGTACCGAGCTCGGATCCACTA-3'    (SEQ ID NO: 5)

5'-ATAGGGCGAATTGGGCCCTCTAGAT-3'    (SEQ ID NO: 6)
```

Amplification reactions (30 µl) were prepared using approximately 50 ng of pCR2.1GH3B as template. In addition, each reaction contained the following components: Fifty picomoles of each of the primers, 1× Taq buffer (New England Biolabs, Beverly, Mass.), 15 pmol each of dATP, dTTP, dGTP, and dCTP, and 0.5 units of Taq DNA polymerase (New England Biolabs, Beverly, Mass., USA). The reactions were incubated in a ROBOCYCLER® programmed for 1 cycle at 94° C. for 1 minute; and 20 cycles each at 94° C. for 30 seconds, 55° C. for 60 seconds, and 72° C. for 1 minute. The heat block then went to a 4° C. soak cycle. The reaction products were isolated on a 2.0% agarose gel using TAE buffer, and a 1 Kb product band was excised from the gel and purified using a QIAQUICK® Gel Extraction Kit (QIAGEN Inc., Valencia, Calif., USA) according to the manufacturer's instructions.

Approximately 40 ng was random-primer labeled using a PRIME-IT® II Kit (Stratagene. La Jolla, Calif., USA) according to the manufacturer's instructions. The radiolabeled gene fragment was separated from unincorporated nucleotide using a MINIELUTE™ PCR Purification Kit (QIAGEN Inc., Valencia, Calif., USA).

The radioactive probe was denatured by adding 5.0 M NaOH to a final concentration of 0.5 M, and added to the hybridization solution at an activity of approximately 0.5× 10$^6$ cpm per ml of hybridization solution. The mixture was incubated for 10 hours at 68° C. in a shaking water bath. Following incubation, the membranes were washed three times in 0.2×SSC, 0.2% SDS at 68° C. The membranes were then dried on blotting paper for 15 minutes, wrapped in SARANWRAP™, and exposed to X-ray film overnight at −80° C. with intensifying screens (Kodak, Rochester, N.Y., USA).

Colonies producing hybridization signals with the probe were inoculated into 1 ml of LB medium supplemented with 100 µg of ampicillin per ml and cultivated overnight at 37° C. Dilutions of each solution were made and 100 µl were plated onto LB agar plates supplemented with 100 µg of ampicillin per ml. The dilution for each positive that produced about 40 colonies per plate was chosen for secondary lifts. The lifts were prepared, hybridized, and probed as above. Two colonies from each positive plate were inoculated into 3 ml of LB medium supplemented with 100 µg of ampicillin per ml and cultivated overnight at 37° C.

Miniprep DNA was prepared from each colony using a BIOROBOT® 9600 (QIAGEN Inc, Valencia, Calif., USA) according to the manufacturers protocol. The size of each insert was determined by Eco RI digestion and agarose gel electrophoresis. One clone designated AF contained an approximately 1.7 kb insert. Sequencing revealed that the clone coded for the expected N-terminal amino acid sequence determined in Example 4, and is hereafter referred to as pKKAF (FIG. 3).

Example 7

Characterization of the *Penicillium brasilianum* Genomic Sequence Encoding Beta-Glucosidase DNA sequencing of the *Penicillium brasilianum* beta-glucosidase gene from pKKAF was performed with an Applied Biosystems Model 3700 Automated DNA Sequencer (Applied Biosystems, Foster City, Calif., USA) using the primer walking technique with dye-terminator chemistry (Giesecke et al., 1992, *J. Virol. Methods* 38: 47-60).

The genomic coding sequence (SEQ ID NO: 1) and deduced amino acid sequence (SEQ ID NO. 2) are shown in FIGS. 1A and 1B. The genomic coding sequence of 1081 by encodes a partial polypeptide of 267 amino acids, interrupted by 4 introns of 92 bp, 63 bp, 72 bp, and 54 bp. The % G+C content of the partial gene is 54.2%. Using the SignalP software program (Nielsen et at, 1997, *Protein Engineering* 10: 1-6), a signal peptide of 19 residues was predicted, corresponding to the signal peptide determined from N-terminal amino acid sequencing.

A search for similar sequences in public databases was carried out with the FASTA program package, version 3.4 (Pearson and D. J. Lipman, 1988, *PNAS* 85:2444, and Pearson, 1990, *Methods in Enzymology* 183:63) using default parameters. A comparative pairwise global alignment of the most similar amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Penicillium brasilianum* GH3B mature partial polypeptide shared 83.1% and 79.6% identity (excluding gaps) to the deduced amino acid sequence of Family 3 glycoside hydrolase proteins from *Thermoascus aurantiacus* (Uniprot Q0ZUL0) and *Talaromyces emersonii* (Uniprot Q8TGI8), respectively.

The present invention is further described by the following numbered paragraphs:

[1] An isolated polypeptide having beta-glucosidase activity, selected from the group consisting of: (a) a polypeptide comprising an amino acid sequence comprising a partial amino acid sequence having at least 85% identity to the partial amino acid sequence of amino acids 20 to 267 of SEQ ID NO: 2: (b) a polypeptide encoded by a polynucleotide comprising a nucleotide sequence comprising a partial nucleotide sequence that hybridizes under at least high stringency conditions with (i) the partial nucleotide sequence of nucleotides 58 to 1081 of SEQ ID NO: 1, (ii) the cDNA sequence contained in the partial nucleotide sequence of nucleotides 58 to 1081 of SEQ ID NO: 1, or (iii) a full-length complementary strand of (i) or (ii); (c) a polypeptide encoded by a polynucleotide comprising a nucleotide sequence comprising a partial nucleotide sequence having at least 85% identity to the partial nucleotide sequence of nucleotides 58 to 1081 of SEQ ID NO: 1: and (d) a variant comprising an amino acid sequence comprising a substitution, deletion, and/or insertion of one or more (several) amino acids of the partial amino acid sequence of amino acids 20 to 267 of SEQ ID NO: 2.

[2] The polypeptide of paragraph 1, comprising an amino acid sequence comprising a partial amino acid sequence having at least 85% identity to amino acids 20 to 267 of SEQ ID NO: 2.

[3] The polypeptide of paragraph 2, comprising an amino acid sequence comprising a partial amino acid sequence having at least 90% identity to amino acids 20 to 267 of SEQ ID NO: 2.

[4] The polypeptide of paragraph 3, comprising an amino acid sequence comprising a partial amino acid sequence having at least 95% identity to amino acids 20 to 267 of SEQ ID NO: 2.

[5] The polypeptide of paragraph 4, comprising an amino acid sequence comprising a partial amino acid sequence having at least 97% identity to amino acids 20 to 267 of SEQ ID NO: 2.

[6] The polypeptide of paragraph 1, comprising an amino acid sequence comprising the partial amino acid sequence of amino acids 20 to 267 of SEQ ID NO: 2; or a fragment thereof having beta-glucosidase activity.

[7] The polypeptide of paragraph 6, comprising a amino acid sequence comprising the partial amino acid sequence of amino acids 20 to 267 of SEQ ID NO: 2.

[8] The polypeptide of paragraph 1, which is encoded by a polynucleotide comprising a nucleotide sequence comprising a partial nucleotide sequence that hybridizes under at least high stringency conditions with (i) the partial nucleotide sequence of nucleotides 58 to 1081 of SEQ ID NO: 1, (ii) the cDNA sequence contained in the partial nucleotide sequence of nucleotides 58 to 1081 of SEQ ID NO: 1, or (iii) a full-length complementary strand of (I) or (ii).

[9] The polypeptide of paragraph 1, which is encoded by a polynucleotide comprising a nucleotide sequence comprising a partial nucleotide sequence having at least 85% identity to the nucleotide sequence of nucleotides 58 to 1081 of SEQ ID NO: 1.

[10] The polypeptide of paragraph 9, which is encoded by a polynucleotide comprising a nucleotide sequence comprising a partial nucleotide sequence having at least 90% identity to the nucleotide sequence of nucleotides 58 to 1081 of SEQ ID NO: 1.

[11] The polypeptide of paragraph 10, which is encoded by a polynucleotide comprising a nucleotide sequence comprising a partial nucleotide sequence having at least 95% identity to the nucleotide sequence of nucleotides 58 to 1081 of SEQ ID NO: 1.

[12] The polypeptide of paragraph 11, which is encoded by a polynucleotide comprising a nucleotide sequence comprising a partial nucleotide sequence having at least 97% identity to the nucleotide sequence of nucleotides 58 to 1081 of SEQ ID NO: 1.

[13] The polypeptide of paragraph 1, which is encoded by a polynucleotide comprising a nucleotide sequence comprising the partial nucleotide sequence of nucleotides 58 to 1081 of SEQ ID NO: 1; or a subsequence thereof encoding a fragment having beta-glucosidase activity.

[14] The polypeptide of paragraph 13, which is encoded by a polynucleotide comprising a nucleotide sequence comprising the partial nucleotide sequence of nucleotides 58 to 1081 of SEQ ID NO: 1.

[15] The polypeptide of paragraph 1, wherein the polypeptide is a variant comprising an amino acid sequence comprising a substitution, deletion, and/or insertion of one or more (several) amino acids of the partial amino acid sequence of amino acids 20 to 267 of SEQ ID NO: 2.

[16] An isolated polynucleotide comprising a nucleotide sequence that encodes the polypeptide of any of paragraphs 1-15.

[17] The isolated polynucleotide of paragraph 16, comprising a nucleotide sequence comprising at least one mutation in the partial nucleotide sequence of nucleotides 58 to 1081 of SEQ ID NO: 1, in which the mutant partial nucleotide sequence encodes the partial amino acid sequence of amino acids 20 to 267 of SEQ ID NO: 2.

[18] A nucleic acid construct comprising the polynucleotide of paragraph 16 or 17 operably linked to one or more (several) control sequences that direct the production of the polypeptide in an expression host.

[19] A recombinant expression vector comprising the nucleic acid construct of paragraph 18.

[20] A recombinant host cell comprising the nucleic acid construct of paragraph 18.

[21] A method of producing the polypeptide of any of paragraphs 1-15, comprising: (a) cultivating a cell, which in its wild-type form produces the polypeptide, under conditions conducive for production of the polypeptide: and (b) recovering the polypeptide.

[22] A method of producing the polypeptide of any of paragraphs 1-15, comprising: (a) cultivating a host cell comprising a nucleic acid construct comprising a nucleotide sequence encoding the polypeptide under conditions conducive for production of the polypeptide: and (b) recovering the polypeptide.

[23] A method of producing a mutant of a parent cell, comprising disrupting or deleting a nucleotide sequence encoding the polypeptide of any of paragraphs 1-15, which results in the mutant producing less of the polypeptide than the parent cell.

[24] A mutant cell produced by the method of paragraph 23.

[25] The mutant cell of paragraph 24, further comprising a gene encoding a native or heterologous protein.

[26] A method of producing a protein, comprising: (a) cultivating the mutant cell of paragraph 25 under conditions conducive for production of the protein; and (b) recovering the protein.

[27] The isolated polynucleotide of paragraph 16 or 17, obtained by (a) hybridizing a population of DNA under at least high stringency conditions with (i) the partial nucleotide sequence of nucleotides 58 to 1081 of SEQ ID NO: 1, (ii) the cDNA sequence contained in the partial nucleotide sequence of nucleotides 58 to 1081 of SEQ ID NO: 1, or (iii) a full-length complementary strand of (i) or (ii); and (b) isolating the hybridizing polynucleotide, which encodes a polypeptide having beta-glucosidase activity.

[28] A method of producing a polynucleotide comprising a mutant nucleotide sequence encoding a polypeptide having beta-glucosidase activity, comprising: (a) introducing at least one mutation into the partial nucleotide sequence of nucleotides 58 to 1081 of SEQ ID NO: 1, wherein the mutant nucleotide sequence encodes a polypeptide comprising an amino acid sequence comprising the partial amino acid sequence of amino acids 20 to 267 of SEQ ID NO: 2; and (b) recovering the polynucleotide comprising the mutant nucleotide sequence.

[29] A mutant polynucleotide produced by the method of paragraph 28.

[30] A method of producing a polypeptide, comprising: (a) cultivating a cell comprising the mutant polynucleotide of paragraph 29 encoding the polypeptide under conditions conducive for production of the polypeptide; and (b) recovering the polypeptide.

[31] A method of producing the polypeptide of any of paragraphs 1-15, comprising: (a) cultivating a transgenic plant or a plant cell comprising a polynucleotide encoding the polypeptide under conditions conducive for production of the polypeptide; and (b) recovering the polypeptide.

[32] A transgenic plant, plant part or plant cell transformed with a polynucleotide encoding the polypeptide of any of paragraphs 1-15.

[33] A double-stranded inhibitory RNA (dsRNA) molecule comprising a subsequence of the polynucleotide of paragraph 16 or 17, wherein optionally the dsRNA is a siRNA or a miRNA molecule.

[34] The double-stranded inhibitory RNA (dsRNA) molecule of paragraph 33, which is about 15, 16, 17, 18, 19, 20, 21, 22, 23, 24, 25 or more duplex nucleotides in length.

[35] A method of inhibiting the expression of a polypeptide having beta-glucosidase activity in a cell, comprising administering to the cell or expressing in the cell a double-stranded RNA (dsRNA) molecule, wherein the dsRNA comprises a subsequence of the polynucleotide of paragraph 16 or 17.

[36] The method of paragraph 35, wherein the dsRNA is about 15, 16, 17, 18, 19, 20, 21, 22, 23, 24, 25 or more duplex nucleotides in length.

[37] A method for degrading or converting a cellulosic material, comprising: treating the cellulosic material with a cellulolytic enzyme composition in the presence of the polypeptide having beta-glucosidase activity of any of paragraphs 1-15, wherein the presence of the polypeptide having beta-glucosidase activity increases the degradation of cellulosic material compared to the absence of the polypeptide having beta-glucosidase activity.

[38] The method of paragraph 37, wherein the cellulosic material is pretreated.

[39] The method of paragraph 37 or 38, wherein the cellulolytic enzyme composition comprises one or more cellulolytic enzymes are selected from the group consisting of a cellulase, endoglucanase, cellobiohydrolase, and beta-glucosidase.

[40] The method of any of paragraphs 37-39, wherein the cellulolytic enzyme composition further comprises a polypeptide having cellulolytic enhancing activity

[41] The method of any of paragraphs 37-40, wherein the cellulolytic enzyme composition further comprises one or more enzymes selected from the group consisting of a hemicellulase, esterase, protease, laccase, or peroxidase.

[42] The method of any of paragraphs 37-41, further comprising recovering the degraded cellulosic material.

[43] The method of paragraph 42, wherein the degraded cellulosic material is a sugar.

[44] The method of paragraph 43, wherein the sugar is selected from the group consisting of glucose, xylose, mannose, galactose, and arabinose.

[45] A method for producing a fermentation product, comprising: (a) saccharifying a cellulosic material with a cellulolytic enzyme composition in the presence of the polypeptide having beta-glucosidase activity of any of paragraphs 1-15, wherein the presence of the polypeptide having beta-glucosidase activity increases the degradation of cellulosic material compared to the absence of the polypeptide having beta-glucosidase activity; (b) fermenting the saccharified cellulosic material of step (a) with one or more fermenting microorganisms to produce the fermentation product; and (c) recovering the fermentation product from the fermentation.

[46] The method of paragraph 45, wherein the cellulosic material is pretreated.

[47] The method of paragraph 45 or 46, wherein the cellulolytic enzyme composition comprises one or more cellu-

[48] The method of any of paragraphs 45-47, wherein the cellulolytic enzyme composition further comprises a polypeptide having cellulolytic enhancing activity.

[49] The method of any of paragraphs 45-48, wherein the cellulolytic enzyme composition further comprises one or more enzymes selected from the group consisting of a hemicellulase, esterase, protease, laccase, or peroxidase.

[50] The method of any of paragraphs 45-49, wherein steps (a) and (b) are performed simultaneously in a simultaneous saccharification and fermentation.

[51] The method of any of paragraphs 45-50, wherein the fermentation product is an alcohol, organic acid, ketone, amino acid, or gas.

[52] A method of fermenting a cellulosic material, comprising: fermenting the cellulosic material with one or more fermenting microorganisms, wherein the cellulosic material is saccharified with a cellulolytic enzyme composition in the presence of a polypeptide having beta-glucosidase activity of any of paragraphs 1-15 and the presence of the polypeptide having beta-glucosidase activity increases the degradation of the cellulosic material compared to the absence of the polypeptide having beta-glucosidase activity.

[53] The method of paragraph 52, wherein the fermenting of the cellulosic material produces a fermentation product.

[54] The method of paragraph 53, further comprising recovering the fermentation product from the fermentation.

[55] The method of any of paragraphs 52-54, wherein the cellulosic material is pretreated before saccharification.

[56] The method of any of paragraphs 52-55, wherein the cellulolytic enzyme composition comprises one or more cellulolytic enzymes selected from the group consisting of a cellulase, endoglucanase, cellobiohydrolase, and beta-glucosidase.

[57] The method of any of paragraphs 52-56, wherein the cellulolytic enzyme composition further comprises a polypeptide having cellulolytic enhancing activity.

[58] The method of any of paragraphs 52-57, wherein the cellulolytic enzyme composition further comprises one or more enzymes selected from the group consisting of a hemicellulase, esterase, protease, laccase, or peroxidase.

[59] The method of any of paragraphs 52-58, wherein the fermentation product is an alcohol, organic acid, ketone, amino acid, or gas.

[60] An isolated polynucleotide encoding a signal peptide comprising or consisting of amino acids 1 to 19 of SEQ ID NO: 2.

[61] A nucleic acid construct comprising a gene encoding a protein operably linked to the polynucleotide of paragraph 60, wherein the gene is foreign to the polynucleotide.

[62] A recombinant expression vector comprising the nucleic acid construct of paragraph 61.

[63] A recombinant host cell comprising the nucleic acid construct of paragraph 61.

[64] A method of producing a protein, comprising: (a) cultivating the recombinant host cell of paragraph 63 under conditions conducive for production of the protein, and (b) recovering the protein.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated polypeptide having beta-glucosidase activity, wherein the polypeptide is selected from the group consisting of:
   (a) a polypeptide comprising an amino acid sequence having at least 95% sequence identity to amino acids 20 to 267 of SEQ ID NO:2;
   (b) a polypeptide encoded by a polynucleotide comprising a nucleotide sequence that hybridizes under at least very high stringency conditions with (i) the nucleotide sequence of nucleotides 58 to 1081 of SEQ ID NO: 1, (ii) a cDNA sequence contained in the nucleotide sequence of nucleotides 58 to 1081 of SEQ ID NO: 1, or (iii) a full-length complementary strand of (i) or (ii); and
   (c) a polypeptide encoded by a polynucleotide comprising a nucleotide sequence having at least 99% sequence identity to nucleotides 58 to 1081 of SEQ ID NO: 1.

2. The polypeptide of claim 1, comprising an amino acid sequence of amino acids 20 to 267 of SEQ ID NO: 2.

3. A nucleic acid construct comprising a nucleotide sequence that encodes the polypeptide of claim 1 operably linked to one or more heteroloqous control sequences that direct the production of the polypeptide in an expression host.

4. A recombinant host cell comprising the nucleic acid construct of claim 3.

5. A method of producing a polypeptide, said method comprising: (a) cultivating an isolated cell which produces the polypeptide of claim 1 under conditions conducive for production of the polypeptide; and (b) recovering the polypeptide.

6. A method of producing a polypeptide, said method comprising: (a) cultivating the recombinant host cell of claim 4 under conditions conducive for production of the polypeptide; and (b) recovering the polypeptide.

7. A method for degrading or converting a cellulosic material, said method comprising treating the cellulosic material with a cellulolytic enzyme composition in the presence of the polypeptide of claim 1, wherein the presence of the polypeptide increases the degradation of cellulosic material compared to the absence of the polypeptide.

8. The method of claim 7, wherein the cellulolytic enzyme composition comprises one or more cellulolytic enzymes selected from the group consisting of a cellulase, endoglucanase, cellobiohydrolase, and beta-glucosidase.

9. The method of claim 7, said method further comprising recovering the degraded cellulosic material.

10. A method for producing a fermentation product, said method comprising:
   (a) saccharifying a cellulosic material with a cellulolytic enzyme composition in the presence of the polypeptide of claim 1, wherein the presence of the polypeptide increases the degradation of cellulosic material compared to the absence of the polypeptide;
   (b) fermenting the saccharified cellulosic material with one or more fermenting microorganisms to produce the fermentation product; and
   (c) recovering the fermentation product from the fermentation.

11. The method of claim 10, wherein the cellulolytic enzyme composition comprises one or more cellulolytic enzymes selected from the group consisting of a cellulase, endoglucanase, cellobiohydrolase, and beta-glucosidase.

12. A method of fermenting a cellulosic material, said method comprising: fermenting the cellulosic material with one or more fermenting microorganisms, wherein the cellulosic material is saccharified with a cellulolytic enzyme composition in the presence of the polypeptide of claim 1 and the presence of the polypeptide increases the degradation of the cellulosic material compared to the absence of the polypeptide.

13. The method of claim 12, wherein the fermenting of the cellulosic material produces a fermentation product.

14. The polypeptide of claim 1, comprising an amino acid sequence having at least 95% sequence identity to amino acids 20 to 267 of SEQ ID NO: 2.

15. The polypeptide of claim 1, comprising an amino acid sequence having at least 97% sequence identity to amino acids 20 to 267 of SEQ ID NO: 2.

16. The polypeptide of claim 1, comprising an amino acid sequence having at least 98% sequence identity to amino acids 20 to 267 of SEQ ID NO: 2.

17. The polypeptide of claim 1, comprising an amino acid sequence having at least 99% sequence identity to amino acids 20 to 267 of SEQ ID NO: 2.

18. A nucleic acid construct comprising a nucleotide sequence that encodes the polypeptide of claim 2, wherein the nucleotide sequence is operably linked to one or more heterologous control sequences that direct production of the polypeptide in an expression host.

19. A recombinant host cell comprising the nucleic acid construct of claim 18.

20. A method of producing a polypeptide said method comprising: (a) cultivating the recombinant host cell of claim 19 under conditions conducive for production of the polypeptide; and (b) recovering the polypeptide.

21. The polypeptide of claim 1, encoded by a polynucleotide comprising a nucleotide sequence that hybridizes under at least very high stringency conditions with the full-length complementary strand of (i) nucleotides 58 to 1081 or SEQ ID NO: 1, or (ii) a cDNA sequence contained in nucleotides 58 to 1081 of SEQ ID NO: 1.

22. The polypeptide of claim 1, encoded by a polynucleotide comprising a nucleotide sequence having at least 99% sequence identity to nucleotides 58 to 1081 of SEQ ID NO: 1.

23. The polypeptide of claim 1, encoded by a polynucleotide comprising a nucleotide sequence of nucleotides 58 to 1081 of SEQ ID NO: 1.

24. A nucleic acid construct comprising a protein coding sequence operably linked to a polynucleotide encoding a signal peptide comprising amino acids 1 to 19 of SEQ ID NO: 2, wherein the protein coding sequence is foreign to the polynucleotide.

25. A recombinant host cell comprising the nucleic acid construct of claim 24.

26. A method of producing a protein, said method comprising: (a) cultivating the recombinant host cell of claim 25 under conditions conducive for production of the protein; and (b) recovering the protein.

* * * * *